US011596812B2

(12) United States Patent
Ebbini

(10) Patent No.: US 11,596,812 B2
(45) Date of Patent: Mar. 7, 2023

(54) WEARABLE TRANSCRANIAL DUAL-MODE ULTRASOUND TRANSDUCERS FOR NEUROMODULATION

(71) Applicant: Regents of the University of Minnesota, Minneapolis, MN (US)

(72) Inventor: Emad S. Ebbini, Edina, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 461 days.

(21) Appl. No.: 16/376,139

(22) Filed: Apr. 5, 2019

(65) Prior Publication Data

US 2019/0308036 A1 Oct. 10, 2019

Related U.S. Application Data

(60) Provisional application No. 62/653,873, filed on Apr. 6, 2018.

(51) Int. Cl.
*A61N 7/00* (2006.01)
*A61B 8/00* (2006.01)
*B06B 1/06* (2006.01)

(52) U.S. Cl.
CPC .............. *A61N 7/00* (2013.01); *A61B 8/4494* (2013.01); *B06B 1/0688* (2013.01);
(Continued)

(58) Field of Classification Search
CPC .............. A61N 7/00; A61N 2007/0086; A61N 2007/0052; A61N 2007/006;
(Continued)

(56) References Cited

U.S. PATENT DOCUMENTS 5,694,936 A 12/1997 Fujimoto
5,906,580 A 5/1999 Kline-Schoder
(Continued)

FOREIGN PATENT DOCUMENTS

CN 101179998 A 5/2008
CN 102788836 A 11/2012
(Continued)

OTHER PUBLICATIONS

Development of an Estimation Instrument of Acoustic Lens Properties for Medical Ultrasound Transducer (Year: 2017).*
(Continued)

*Primary Examiner* — Hien N Nguyen
(74) *Attorney, Agent, or Firm* — Mueting Raasch Group

(57) ABSTRACT

An ultrasound transducer array is incorporated in a lightweight, conformable, and wearable patch that may be used to deliver, monitor, and control localized transcranial focused ultrasound (tFUS). The patch may include full-duplex transmit-receive circuitry that may be used for continuous monitoring of transcranial focused ultrasound (tFUS) application. The circuitry may include a circulator. The ultrasound transducer array may be coupled to an aperture interface having irregularly sized or shaped channel conductors to provide a coarse aperture for the array. The coarse aperture may be designed using a method that provides a reduced channel count.

12 Claims, 14 Drawing Sheets

(52) U.S. Cl.
CPC ..... *A61N 2007/006* (2013.01); *A61N 2007/0026* (2013.01); *A61N 2007/0052* (2013.01); *A61N 2007/0086* (2013.01)

(58) Field of Classification Search
CPC .......... A61N 2007/0026; A61B 8/4494; A61B 8/0808; A61B 8/4236; B06B 1/0688; B06B 1/0223
See application file for complete search history.

(56) References Cited

U.S. PATENT DOCUMENTS

| | | |
|---|---|---|
| 6,277,075 B1 | 8/2001 | Torp |
| 6,172,939 B1 | 10/2001 | Cole |
| 6,318,179 B1 | 11/2001 | Hamilton et al. |
| 6,492,762 B1 | 12/2002 | pant |
| 6,494,839 B1 | 12/2002 | Averkiou |
| 6,540,677 B1 | 4/2003 | Angelson |
| 6,618,493 B1 | 9/2003 | Torp |
| 6,705,993 B2 | 3/2004 | Ebbini |
| 6,770,031 B2 | 8/2004 | Hynynen et al. |
| 6,951,540 B2 | 10/2005 | Ebbini et al. |
| 7,063,666 B2 | 6/2006 | Weng et al. |
| 7,686,764 B2 | 3/2010 | Watanabe et al. |
| 7,901,358 B2 | 3/2011 | Mehi |
| 8,002,705 B1 | 8/2011 | Napolitano |
| 8,086,296 B2 | 12/2011 | Bystritsky |
| 8,591,419 B2 | 11/2013 | Tyler |
| 8,911,372 B2 | 12/2014 | Yoshikawa et al. |
| 8,939,909 B2 | 1/2015 | Wegner |
| 9,144,693 B2 | 9/2015 | Appelman |
| 9,592,409 B2 | 3/2017 | Yoo |
| 9,610,061 B2 | 4/2017 | Ebbini et al. |
| 10,231,712 B2 | 3/2019 | Ebbini et al. |
| 10,973,494 B2 * | 4/2021 | Koski ............... B06B 1/0622 |
| 2001/0017937 A1 | 5/2001 | Bonnefous |
| 2001/0029336 A1 | 10/2001 | Teo |
| 2001/0039381 A1 | 11/2001 | Burns et al. |
| 2003/0036702 A1 * | 2/2003 | Davidsen ............ B06B 1/0622 |
| | | 600/437 |
| 2003/0097068 A1 | 5/2003 | Hossack |
| 2003/0220636 A1 | 11/2003 | Bowman |
| 2003/0225331 A1 | 12/2003 | Diederich |
| 2004/0015079 A1 | 1/2004 | Berger |
| 2004/0106880 A1 | 6/2004 | Weng |
| 2004/0210135 A1 | 10/2004 | Hynynen |
| 2005/0070796 A1 | 3/2005 | Tsujita |
| 2005/0102009 A1 | 5/2005 | Costantino |
| 2005/0249667 A1 | 11/2005 | Tuszynski |
| 2005/0267453 A1 | 12/2005 | Wong et al. |
| 2007/0016040 A1 | 1/2007 | Nita |
| 2007/0038100 A1 | 2/2007 | Nita |
| 2007/0055155 A1 | 3/2007 | Owen |
| 2007/0129633 A1 | 6/2007 | Lee et al. |
| 2008/0015440 A1 | 1/2008 | Shandas |
| 2008/0027320 A1 | 1/2008 | Bolorforosh |
| 2008/0045882 A1 | 2/2008 | Finsterwald |
| 2008/0221448 A1 | 9/2008 | Khuri-Yakub et al. |
| 2008/0228075 A1 | 9/2008 | Fraser |
| 2009/0048546 A1 | 2/2009 | Appelman et al. |
| 2009/0069677 A1 | 3/2009 | Chen |
| 2009/0069680 A1 | 3/2009 | Yasuhiko |
| 2010/0004540 A1 | 1/2010 | Thiele |
| 2010/0286520 A1 | 11/2010 | Hazard |
| 2011/0112405 A1 | 5/2011 | Barthe |
| 2011/0248714 A1 | 10/2011 | Salomir |
| 2012/0053391 A1 | 3/2012 | Mishelevich |
| 2012/0083692 A1 | 4/2012 | Stoll |
| 2012/0283502 A1 | 8/2012 | Mishelevich |
| 2012/0283564 A1 | 11/2012 | Ebbini |
| 2012/0289869 A1 | 11/2012 | Tyler |
| 2013/0123635 A1 | 5/2013 | Wegner |
| 2013/0144165 A1 | 6/2013 | Ebbini et al. |
| 2013/0197368 A1 * | 8/2013 | Jin ................. A61B 8/4444 |
| | | 600/459 |
| 2014/0343463 A1 | 11/2014 | Mishelevich |
| 2015/0251025 A1 | 9/2015 | You |
| 2016/0143617 A1 | 5/2016 | Ebbini et al. |
| 2017/0080255 A1 | 3/2017 | Law |
| 2017/0224990 A1 | 8/2017 | Goldwasser |
| 2017/0296140 A1 | 10/2017 | Ebbini |
| 2019/0160309 A1 | 5/2019 | Ebbini |
| 2019/0269385 A1 | 9/2019 | Ebbini et al. |
| 2020/0121960 A1 | 4/2020 | Darrow et al. |

FOREIGN PATENT DOCUMENTS

| | | |
|---|---|---|
| CN | 102800071 A | 11/2012 |
| EP | 0392743 A1 | 10/1990 |
| EP | 2310094 B1 | 10/2014 |
| WO | WO 2006/018761 A1 | 2/2006 |
| WO | WO 2006/042201 A1 | 4/2006 |
| WO | WO 2006/090298 A1 | 8/2006 |
| WO | WO 2008/053457 A2 | 5/2008 |
| WO | WO 2009/002492 A1 | 12/2008 |
| WO | WO 2009/050719 A2 | 4/2009 |
| WO | WO 2011/156624 A2 | 12/2011 |
| WO | WO 2012/033584 A2 | 3/2012 |
| WO | WO 2012/142455 A2 | 10/2012 |
| WO | WO 2013/059833 A1 | 4/2013 |
| WO | WO 2015/013196 A2 | 1/2015 |

OTHER PUBLICATIONS

Ainsworth, "3D ultrasound measurement of change in carotid plaque volume—A tool for rapid evaluation of new therapies," 2005. *Stroke.* 36(9):1904-1909.

Aldiabat, "Real-Time Image-Based Transcranial Refocusing of Dual-Mode Ultrasound Arrays" Dissertation, Jan. 2019, 161 pages.

Alonso, "Focal delivery of AAV2/1-transgenes into the rat brain by localized ultrasound-induced BBB opening" 2013 *Mol Ther Nucleic Acids*, 2:e73.

Amini, "Noninvasive Estimation of Tissue Temperature Via High-Resolution Spectral Analysis Techniques," Feb. 2005 *IEEE Transactions on Biomedical Engineering*, 52(2):221-228.

Arthur, "In vivo change in ultrasonic backscattered energy with temperature in motion-compensated images," 2008 *International Journal of Hyperthermia*, 24(5):389-398.

Arvanitis, "Combined ultrasound and mr imag-ing to guide focused ultrasound therapies in the brain" Jul. 2013 *Phys Med Biol*, 58(14):4749-4761.

Aryal, "Multiple treatments with liposomal doxorubicin and ultrasound-induced disruption of blood-tumor and blood-brain barriers improve outcomes in a rat glioma model" Jul. 2013 *J Control Release*, 169(1-2):103-111.

Aubry, "Experimental demonstration of noninvasive transskull adaptive focusing based on prior computed tomography scans" 2013 *The Journal of the Acoustical Society of America*, 113(1):84-93.

Aubry, "Transcostal high-intensity-focuses ultrasound: Ex vivo adaptive focusing feasibility study," 2008 *Phys. Med. Biol.*, 53:2937-2951.

Baek, "A review of low-intensity focused ultrasound for neuromodulation" 2017 *Biomed. Eng. Lett.* 7:135-142.

Baker, "A review of therapeutic ultrasound: biophysical effects" 2001 *Phys. Ther.* 81, 1351-1358.

Bakker, "The scalable brain atlas: Instant web-based access to public brain atlases and related content" 2015 *Neuroinformatics*, 13(3):353-366.

Ballard, "Adaptive transthoracic refocusing of dual-mode ultrasound arrays" Jan. 2010 *IEEE Trans Bionred Eng.*, 57(1): 93-102.

Ballard, "Monitoring and Guidance of HIFU Beams with Dual-Mode Ultrasound Arrays," *31st Annual International Conference of the IEEE EMBS*, Minneapolis, MN; Sep. 2-6, 2009:137-140.

Ballard, "Dual-mode ultrasound arrays for image-guided targeting of atheromatous plaques" in *AIP Conference Proceedings* 1503, 124-128 (AIP, 2012).

Barber, "The density of tissues in and about the head" 1970 *Acta neurologica scandinavica*, 46(1):85-92.

(56) References Cited

OTHER PUBLICATIONS

Barnard, "Small localized ultrasonic lesions in the white and gray matter of the cat brain" 1956 *AMA Archives of Neurology & Psychiatry*, 75(1): 15-35.
Bayat, "Adaptive motion compensation for in vivo ultrasound temperature estimation" in Ultrasonics Symposium (IUS), 2013 IEEE International, pp. 1797-1800.
Bayat, "Ultrasound thermography in vivo: A new model for calculation of temperature change in the presence of temperature heterogeneity" in 2013 *IEEE International Ultrasonics Symposium (IUS)*, pp. 116-119 (ieeexplore.ieee.org, 2013).
Bischof, "Rectal Protection During Prostate Cryosurgery: Design and Characterization of an Insulating Probe," 1997 *Cryobiology*, 34:80-92.
Blake, "A Method to estimate wall shear rate with a clinical ultrasound scanner" 2008 *Ultrasound in Medicine and Biology*, 34(5):760-774.
Blana, "First analysis of the long-term results with transrectal HIFU in patients with localized prostate cancer" Jun. 2008 *Euro Urology*, 53(6):1194-1203.
Bohn, "An analysis package comparing PID anti-windup strategies" Apr. 1995 *Control Systems Magazine*, IEEE, 15(2):34-40.
Botros, "A Hybrid Computational Model for Ultrasound Phased-Array Heating in Presence of Strongly Scattering Obstacles" Nov. 1997 IEEE Trans Biomed Eng., 44(11): 1039-1050.
Botros, "Two-step hybrid virtual array-ray (VAR) technique for focusing through the rib cage," Jul. 1998 *IEEE Trans. Ultrason. Ferroelectr., Freq. Control*, 45(4):989-1000.
Bracewell, "Two-dimensional Imaging" Prentice-Hall Signal Processing Series. 1995. Cover page, Title Page, Copyright Page, and Table of Contents. 11 pages total.
Burgess, "Targeted delivery of neural stem cells to the brain using mri-guided focused ultrasound to disrupt the blood-brain barrier" 2011 *PLoS One*, 6(11):e27877.
Byrne, "Epidural cylinder electrodes for presurgical evaluation of intractable epilepsy: technical note" Aug. 2008 Surg Neurol., 70(2):160-4; discussion 164. doi: 10.1016/j.surneu.2007.04.024. Epub Feb. 8, 2008.
Bystristsky, A review of low-intensity transcranial focused ultrasound for clinical applica-tions. *Curr Behav Neurosci*, 2:60-66, 2015.
Bystritsky, A review of low-intensity focused ultrasound pulsation. *Brain Stimul*, 4(3):125-136, Jul. 2011.
Casper, "Realtime Control of Multiple-focus Phased Array Heating Patterns Based on Noninvasive Ultrasound Thermography," 2010 *IEEE International Ultrasonics Symposium Proceedings*, pp. 467-470.
Casper, "Realtime Control of Multiple-focus Phased Array Heating Patterns Based on Noninvasive Ultrasound Thermography," Jan. 2012 *IEEE Trans. Biomed. Eng.*, 59(1):95-105.
Casper, "Real-time implementation of a dual-mode ultrasound array system: In vivo results" 2013 IEEE Transactions on Biomedical Engineering, 60(10):2751-2759.
Cespedes, "Echo decorrelation from displacement gradients in elasticity and velocity estimation" 1999 *IEEE Trans. UFFC.*, 46:791-801.
Chan, "Laser-generated focused ultrasound for arbitrary waveforms" 2016 *Appl. Phys. Lett.*, 109:174102.
Chan, "An image-guided high intensity focused ultrasound device for uterine fibroids treatment," 2002 *Med. Phys.*, 29:2611-2620.
Chan, Chapter 2 "Basics of Ultrasound Imaging" Narouze (Ed.), Atlas of Ultrasound-Guided Procedures in Interventional Pain Management, Springer: New York, NY; 2011. Cover page, publisher's page, and pp. 13-19.
Chang, "Unilateral magnetic resonance guided focused ultrasound thalamotomy for essential tremor: practices and clinicoradiological outcomes" 2015 *J Neurol Neurosurg Psychiatry*, 86(3):257-264.
Chapelon, "New piezoelectric transducers for therapeutic ultrasound," Jan. 2000 *Ultrasound Med. Biol.*, 26(1):153-159.
Chew, Waves and Fields in Inhomogenous Media, Van Nostrand Reinhold: New York; 1990. Cover Page, Title Page, Copyright Page, and Table of Contents. 12 pages total.
Chiao, "Coded excitation for diagnostic ultrasound: A system developer's perspective" Feb. 2005 IEEE Trans. *Ultrason., Ferroelect., Freq. Colllr.*, 52(2):160-170.
Chu, "Neuromodulation Accompanying Focused Ultrasound-Induced Blood-Brain Barrier Opening" Oct. 2015 *Scientific Reports* 5:15477; 12 pages.
Clement, "A noninvasive method for focusing ultrasound through the human skull" 2002 *Phys Med Biol.*, 47: 1219-1236.
Coluccia, "First noninvasive thermal ablation of a brain tumor with MR-guided focused ultrasound," 2014, *J Ther Ultrasound*, 2:17.
Constans, "A 200-1380-kHz Quadrifrequency Focused Ultrasound Transducer for Neurostimulation in Rodents and Primates: Transcranial In Vitro Calibration and Numerical Study of the Influence of Skull Cavity" 2017 *IEEE Trans Ultrason Ferroelectr Freq Control.*, 64(4):717-724. doi: 10.1109/TUFFC.2017.2651648. Epub Jan. 11, 2017.
Corl, "A real-time synthetic-aperture imaging system" in Acoustical Imaging vol. 9 Visualization and Characterization, 1980, Plenum Press. Cover page, copyright page and pp. 341-355.
Curiel, "1.5-D high intensity focused ultrasound array for non-invasive prostate cancer surgery," Feb. 2002 *IEEE Trans. Ultrason., Ferroelectr., Freq. Control*, 49(2):231-242.
Dallapiazza, "Noninvasive neuromodulation and thalamic mapping with low-intensity focused ultrasound" Apr. 2017 *J Neurosurg.*, 1-10. doi: 10.3171/2016.11.JNS16976. [Epub ahead of print].
Dalong, "Viscoelastic property measurement in thin tissue constructs using ultrasound," 2008 *IEEE Trans. Ultrason. Ferroelecdt. Freq. Contr.*, 55(2):368-383.
Daniels, "Focused Ultrasound-Induced Suppression of Auditory Evoked Potentials in Vivo" 2018 *Ultrasound Med. Biol.* 44, 1022-1030.
Darrow, "Reversible neuroinhibition by focused ultrasound is mediated by a thermal mechanism" Nov.-Dec. 2019 *Brain Stimul.*, 12(6):1439-1447. doi: 10.1016/j.brs.2019.07.015. Epub Jul. 23, 2019. Prepublication.
Darrow, "Transcranial Focused Dual-Mode Ultrasound for Noninvasive Neuromodulation" presentation Sep. 30, 2018, Minnesota Neurological Society meeting; 34 pages.
Darvas, "Toward Deep Brain Monitoring with Superficial EEG Sensors Plus Neuromodulatory Focused Ultrasound" Aug. 2016, *Ultrasound Med Biol.*, 42(8):1834-47. doi: 10.1016/j.ultrasmedbio. 2016.02.020. Epub May 13, 2016.
Davies, "Pulse wave analysis and pulse wave velocity: A critical review of their strengths and weaknesses" Mar. 2003 *J Hypertens.*, 21(3):463-72.
Deffieux, "Low-intensity focused ultrasound modulates monkey visuomotor behavior" 2013 *Current Biology*, 23(23):2430-2433.
Deng, "Targeted drug delivery across the blood-brain barrier using ultrasound technique" Dec. 2010 *Ther Deliv*, 1(6):819-848.
Dumas, "Piezocomposite technology an innovative approach to the improvement of ndt performance using ultrasounds" in 8th European Conference on Non Destructive Testing, Jun. 2002, Barcelona, Spain; 2 pages.
Dunmire, "Cross-beam vector doppler ultrasound for angle-independent velocity measurements" Oct. 2000 *Ultrasound Med Biol.*, 26(8):1213-1235.
Ebbini, "A cylindrical-section ultrasound phased-array applicator for hyperthermia cancer therapy," 1988 *IEEE Trans. Ultrasonics, Ferroelectrics, and Frequency Control*, 35(5):561-572.
Ebbini, "Deep-localized hyperthermia with ultrasound phased arrays using the pseudoinverse pattern synthesis methods," Ph.D. Dissertation, University of Illinois, Urbana, IL, 1990, 24 pages.
Ebbini, "Dereverberation of ultrasound echo data in vascular imaging applications" 2011, *ICASSP, IEEE International Conference on Acoustics, Speech and Signal Processing—Proceedings*. 2011: 741-744.
Ebbini, "Dual-mode ultrasound phased arrays for image-guided surgery" Apr. 2006 *Ultrasonic Imaging*, 28(2):65-82.

(56) References Cited

OTHER PUBLICATIONS

Ebbini, "Experimental evaluation of a prototype cylindrical section ultrasound hyperthermia phased-array applicator," Sep. 1991 *IEEE Transactions on Ultrasonics Ferroelectrics and Frequency Control*, 38(5):510-520.
Ebbini, "Fundamental resolution limits of a coded-excitation system for real-time pulse-echo imaging" in Nov. 1997 Proceedings of the IEEE Ultrasonics Symposium 2, 1997(2):1539-1542.
Ebbini, "Guest Editorial to the Special Issue on Therapeutic Ultrasound: Current Status and Future Directions," Jan. 2010 *IEEE Transactions on Biomedical Engineering*, 57(1):57-60.
Ebbini, "Guest Editorial to the Special Issue on Therapeutic Ultrasound: Trends at the Leading-Edge," *IEEE Transactions on Biomedical Engineering*, Jan. 2010; 57(1):5-6.
Ebbini, "Lesion formation and visualization using dual-mode ultrasound phased arrays," Oct. 2001 *Proc. IEEE Ultrason. Symp.*, 2:1351-1354.
Ebbini, "Monitoring and Guidance of Minimally-Invasive Thermal Therapy Using Diagnostic Ultrasound," *31st Annual International Conference of the IEEE EMBS*, Minneapolis, MN; Sep. 2-6, 2009:4283-4286.
Ebbini, "Multiple-focus ultrasound phased-array pattern synthesis: optimal driving-signal distributions for hyperthermia" Sep. 1989 IEEE Trans Ultrason Ferroelectr Freq Control., 36(5):540-8.
Ebbini, "A new Svd-based optimal inverse filter design for ultrasonic applications" in Ultrasonics Symposium, 1993. Proceedings., IEEE, 2:1187-1190.
Ebbini, "Optimal transversal filter bank for 3d real-Lime acoustical imaging" in Signals, Systems and Computers, 1992 Conference Record of The Twenty-Sixth Asilomar Conference 011, 2:831-835.
Ebbini, "Optimization of the intensity gain of multiple-focus phased-array heating patterns," 1991 *Int. J. Hyperthermia*, 7(6): 953-973.
Ebbini, "Phase-coupled two-dimensional speckle tracking algorithm" May 2006 IEEE Trans Ultrason Ferroelectr Freq Control., 53(5):972-90.
Ebbini, "Real-time ultrasound thermography and thermometry [life sciences]" Mar. 2018 IEEE Signal Processing Magazine, 35:166-174.
Ebbini, "Region-adaptive motion tracking of speckle imagery" 2000 ICASSP, IEEE International Conference on Acoustics, Speech and Signal Processing—Proceedings. 4:2075-2078.
Ebbini, "A spherical-section ultrasound phased array applicator for deep localized hyperthermia," Jul. 1991 *IEEE Trans. Biomedical Engineering*, 38(7):634-643.
Elias, "A randomized trial of focused ultrasound thalamotomy for essential tremor" Aug. 2016, *New England Journal of Medicine*, 375(8):730-9.
European Search Report and Search Opinion for European Patent Application No. 18193572.7, dated Sep. 2, 2019, 15 pages.
Figueroa, "A Computational Framework for Fluid-Solid-Growth Modeling in Cardiovascular Simulations" Sep. 2009 *Comput Methods Appl Mech Eng.*, 198(45-46):3583-3602.
Fink, "Time reversal of ultrasonic fields. I. Basic principles," Sep. 1992 *IEEE Trans. Ultrason., Ferroelectr., Freq. Control*, 39(5):555-566.
Fisher, "Low-intensity focused ultrasound alters the latency and spatial patterns of sensory-evoked cortical responses in vivo" 2018 *J. Neural Eng.* 15, 035004.
Fleury, "New piezocomposite transducers capable of producing high-power levels suitable for therapy with reasonably wide bandwidth suitable for imaging," 2002 *Proc. 2nd Int. Symp. Ther. Ultrasound*, 1:428-436.
Fry, "Ultrasonic lesions in the mammalian central nervous system" 1955, *Science*, 122(3168):517-518.
Fry, "Acoustical properties of the human skull" 1978 *The Journal of the Acoustical Society of America*, 63(5):1576-1590.
Fry, "Fundamental neurological research and human neurosurgery using intense ultrasound" 1960 *IRE transactions on medical electronics*, 3:166-181.
Fry, "Further studies of the transkull transmission of an intense focused ultrasonic beam: lesion production at 500 khz" 1980 *Ultrasound Med Biol*, 6(1):33-38.
Fry, "Production of focal destructive lesions in the central nervous system with ultrasound" 1954 *Journal of neurosurgery*, 11(5):471-478.
Fry, "Production of reversible changes in the central nervous system by ultrasound" 1958 *Science*, 127(3289):83-84.
Fry, "Transkull transmission of an intense focused ultrasonic beam" 1977 *Ultrasound in Medicine and Biology*, 3(2):183-184.
Fry, "Transkull focal lesions in cat brain produced by ultrasound" May 1981 *J Neurosurg*, 54(5):659-663.
Fung, Biomechanics: Circulation, $2^{nd}$ Ed. Springer, New York. 1997. Cover Page, Copyright Page, Table of Contents.
Gelet, "845 Prostate cancer control with transrectal HIFU in 242 consecutive patients: 5-year results" Jan. 2004 *European Urology Supplements* 3(2):214-214.
Goel, "Adjuvant Approaches to Enhance Cryosurgery," Jul. 2009 *Journal of Biomechanical Engineering*, 131(7):074003.
Golemati, "Carotid artery wall motion estimated from b-mode ultrasound using region tracking and block matching" 2003 *Ultrasound in Med & Biol.*, 29(3):387-399.
Goodman, "*Introduction to Fourier Optics*" 2005, Roberts & Company, Greenwood Village, Colorado. Cover page, publisher page, table of contents.
Gronningsaeter, "Vessel wall detection and blood noise reduction in intravascular ultrasound imaging," May 1996; *IEEE Transactions on Ultrasonics, Ferroelectrics and Frequency Control, IEEE, US*, 43(3):359-369.
Gulick, "Comparison of Electrical and Ultrasound Neurostimulation in Rat Motor Cortex" 2017 *Ultrasound Med. Biol.*, 43:2824-2833.
Gulick, "Effect of Ultrasound Stimulation on Excised Brain Tissue Impedance" 2013 *IEEE Neural Engineering Short Papers* No. 0669', 1 page.
Guo, "Ultrasound Produces Extensive Brain Activation via a Cochlear Pathway" 2018 *Neuron* 98:1020-1030.e4.
Haddadin, "Imaging Strongly Scattering Media Using Multiple-frequency Distorted Born Iterative Method," 1998 I*EEE Trans. UFFC*, 5(6):1485-1496.
Haddadin, "Ultrasonic focusing through inhomogeneous media by application of the inverse scattering problem" Jul. 1998, *J Acoust Soc Am.*, 104(1): 313-325.
Haken, "Effect of mode conversion on ultrasonic heating oat tissue interfaces," 1992 *J. Ultrasound Med.*, 11:393-405.
Hakimova, "Ultrasound stimulation inhibits recurrent seizures and improves behavioral outcome in an experimental model of mesial temporal lobe epilepsy" Aug. 2015 *Epilepsy Behav*, 49:26-32.
Hall, "Phantom materials for elastography" 1997 *IEEE transactions on ultrasonics, ferroelectrics, and frequency control*, 44(6):1355-1365.
Hameroff, "Transcranial ultrasound (TUS) effects on mental states: a pilot study" May 2013 *Brain Stimul.*, 6(3):409-15. doi: 10.1016/j.brs.2012.05.002. Epub May 29, 2012.
Haritonova, "In vivo application and localization of transcranial focused ultrasound using dual-mode ultrasound arrays" 2015 *IEEE transactions on ultrasonics, ferroelectrics, and frequency control*, 62(12):2031-2042.
Hermus, "Advanced carotid plaque imaging" 2010 *European Journ. Of Vascular and Endovascular Surgery*, 39(2):125-133.
Hindley, "MRI guidance of focused ultrasound therapy of uterine fibroids: Early results," Dec. 2004 *Am. J. Roentgenology*, 183(6):1713-1719.
Hirata, "Pulse wave analysis and pulse wave velocity: a review of blood pressure interpretation 100 years after Korotkov" Oct. 2006 *Circ J.*, 70(10):1231-9.
Hynynen, "Demonstration of potential noninvasive ultrasound brain therapy through an intact skull" 1998 *Ultrasound in medicine & biology*, 24(2):275-283.
Hynynen, "MR imaging-guided focused ultrasound surgery of fibroadenomas in the breast: a feasibility study" 2001 *Radiology*, 219(1):176-185.

(56) References Cited

OTHER PUBLICATIONS

Hynynen, "Noninvasive MR imaging-guided focal opening of the blood-brain barrier in rabbits" Sep. 2001 *Radiology*, 220(3):640-646.

Hynynen, "Pre-clinical testing of a phased array ultrasound system for mri-guided noninvasive surgery of the braina primate study" 2006 *European journal of radiology*, 59(2):149-156.

Hynynen, "Trans-skull ultrasound therapy: The feasibility of using image-derived skull thickness information to correct the phase distortion," May 1999 *IEEE Trans. Ultrason, Ferroelectr., Freq. Control*, 46(5):752-755.

Hynynen, "Ultrasound for drug and gene delivery to the brain" Jun. 2008 *Adv Drug Deliv Rev*, 60(10):1209-1217.

Hynynen, "500-element ultrasound phased array system for noninvasive focal surgery of the brain: a preliminary rabbit study with ex vivo human skulls" 2004 *Magn. Reson. Med.*, 52:100-107.

Hyungmin, "Estimation of the spatial profile of neuromodulation and the temporal latency in motor responses induced by focused ultrasound brain stimulation" May 2014 *Neuroreport*, 25(7):475-479.

Ibbini, "N×N square-element ultrasound phased array applicator: Simulated temperature distributions associated with directly synthesized heating patterns," 1990 *IEEE Trans. Ultrason, Ferroelectr., Freq. Control*, 37(6):491-500.

Insana, "Maximum-likelihood approach to strain imaging using ultrasound" 2000 *J. Acoust. Soc. Am.*, 107(3):1421-1434.

International Written Opinion/International Preliminary Report on Patentability, dated Jul. 15, 2009 for International Patent Application No. PCT/US2008/007842, 25 pgs.

International Preliminary Report on Patentability dated Feb. 4, 2016 for International Patent Application No. PCT/US2014/047430, 13 pages.

International Preliminary Report on Patentability dated Oct. 15, 2013, for International Patent Application No. PCT/US2012/033584, 12 pgs.

International Preliminary Report on Patentability dated Dec. 10, 2012, for International Patent Application No. PCT/US2011/039837, 6 pgs.

International Search Report dated Jun. 13, 2013 for International Patent Application No. PCT/US2012/033584, 6 pgs.

International Search Report dated Jan. 20, 2012, for International Patent Application No. PCT/US2011/039837, 4 pgs.

International Search Report dated Jan. 20, 2015 for International Patent Application No. PCT/US2014/047430, 16 pgs.

Ishida, "Development and animal experiment of variable focusing HIFU system for prostate cancer treatment," 2003 *3rd Int. Symp. THer. Ultrasound*, 1:382-387.

Jedrzejewicz, "Two-way continuous transmit and receive focusing in ultrasound imaging" 2013 ZONARE Medical Systems, Inc., Tech. Rep., [Online], Available: http://res.mindray.com/Documents/2016-12-14/d2dd8ebd-a052-482a-8541-b8de227d4ee6/K90127_two_way_transmit_receive.pdf.

Jensen, "Calculation of pressure fields from arbitrarily shaped, apodized, and excited ultrasound transducers" 1992 *IEEE transactions on ultrasonics, ferroelectrics, and frequency control*, 39(2):262-267.

Jensen, "Synthetic aperture ultrasound imaging" 2006 *Ultrasonics*, 44:e5-e15.

Jones, "Comparison of analytical and numerical approaches for ct-based aberration correction in transcranial passive acoustic imaging" 2015 *Physics in Medicine & Biology*, 61(1): 23.

Jossinet, "Impedance Modulation by Pulsed Ultrasound" 1999 *Annals of the New York Academy of Sciences* 873 (1 ELECTRICAL BI):396-407.

Kamimura, "Focused ultrasound neuromodulation of cortical and subcortical brain structures using 1.9 MHz" 2016 *Med. Phys.* 43, 5730.

Karimi, "Estimation of Nonlinear Mechanical Propenics of Vascular Tissues via Elastography" Dec. 2008 *Cardiovasc Eng.*, 8(4):191-202. doi: 10.1007/s10558-008-9061-0.

Khanna, "Intracranial Applications of MR Imaging-Guided Focused Ultrasound" 2011 *AJNR Am. J. Neuroradiol*. doi: 10.3174/ajnr.A4902, 426-431.

Khraiche, "Ultrasound induced increase in excitability of single neurons" 2008 *Conf Proc IEEE Eng Med Biol Soc.* 2008:4246-9. doi: 10.1109/IEMBS.2008.4650147.

Kim, "Arterial vulnerable plaque characterization using ultrasound-induced thermal strain imaging (TSI)," 2008 *IEEE Transaction on Biomedical engineering*, 55(1):171-180.

Kim, "Estimation of the spatial profile of neuromodulation and the temporal latency in motor responses induced by focused ultrasound brain stimulation" 2014 *Neuroreport*, 25(7):475.

Kim "Focused ultrasound-mediated non-invasive brain stimulation: examination of sonication parameters" 2014 *Brain Stimul.*, 7(5):748-56. doi: 10.1016/j.brs.2014.06.011. Epub Jul. 2, 2014.

Kim, "Noninvasive transcranial stimulation of rat abducens nerve by focused ultrasound" *Ultrasound in medicine & biology*, 38, No. 9, pp. 1568-1575, 2012.

Kim, "Suppression of EEG visual-evoked potentials in rats through neuromodulatory focused ultrasound" 2015 *Neuroreport* 26:211-215.

King, "Effective parameters for ultrasound-induced in vivo neurostimulation" *Ultrasound in medicine & biology*, 39, No. 2, pp. 312-331, 2013.

King, "Localization of ultrasound induced in vivo neurostimulation in the mouse model" *Ultrasound in medicine & biology*, 40, No. 7, pp. 1512-1522, 2014.

Kinoshita, "Noninvasive localized delivery of herceptin to the mouse brain by mri-guided focused ultrasound-induced blood-brain barrier disruption" *Proceedings of the National Academy of Sciences*, 2006, 103(31):11719-11723.

Konofagou, "Optimization of the ultrasound-induced blood-brain barrier opening" 2012 *Theranostics*, 2(12):1223-1237.

Krishna, "Prospective Tractography-Based Targeting for Improved Safety of Focused Ultrasound Thalamotomy" 2018 *Neurosurgery*. doi:10.1093/neuros/nyy020.

Kyriakou, "A review of numerical and experimental compensation techniques for skull-induced phase aberrations in transcranial focused ultrasound" 2014 *Int. J. Hyperthermia* 30:36-46.

Lalonde, "Field conjugate acoustic lenses for ultrasound hyperthermia" Sep. 1993 *IEEE Transactions on Ultrasonics, Ferroelectrics, and Frequency Control*, 40(5):592-602.

Lalonde, "Variable frequency field conjugate lenses for ultrasound hyperthermia" Sep. 1995 *IEEE Transactions on Ultrasonics, Ferroelectrics, and Frequency Control*, 42(5):825-831.

Lee, "High Intensity Focused Ultrasound Effect on Cardiac Tissues: Potential for Clinical Application," 2000 *Echocardiography*, 17(6):563-566.

Legon, "Neuromodulation with single-element transcranial focused ultrasound in human thalamus" 2018 *Hum. Brain Mapp.* 39, 1995-2006.

Legon, "Transcranial focused ultrasound modulates the activity of primary somatosensory cortex in humans" 2014 *Nature Neurosci.*, 17(2):322-329.

Legon, "Transcranial focused ultrasound neuromodulation of the human primary motor cortex" 2018 *Sci. Rep.* 8:10007.

Lele, "The thermal hypothesis of the mechanism of ultrasonic focal destruction in organized tissues" Interaction of ultrasound and biological tissues. FDA, pp. 73-8008, 1972.

Li, "A new filter design technique for coded excitation systems," 1992 *IEEE Trans. Ultrasonics, Ferroelectrics, and Frequency Control*, 39(6):693-699.

Li, "Blocked Element Compensations in Phased Array Imaging," 1993 *IEEE Trans. Ultrasonics, Ferroelectrics, and Frequency Control*, 40(4):283-292.

Lindsey, "Simultaneous bilateral real-time 3-d transcranial ultrasound imaging at 1 {MHz} through poor acoustic windows" 2013 *Ultrasound in Medicine and Biology*, 39(4) 721-734, 2013.

Lipsman, "MR-guided focused ultrasound thalamotomy for essential tremor: a proof-of-concept study" 2013 *The Lancet Neurology*, 12(5):462-468.

Liu, "Adaptive lesion formation using dual mode ultrasound array system" 2017 *AIP Conf. Proc.* 1821, 060003.

(56) References Cited

OTHER PUBLICATIONS

Liu, "In vivo mr quantification of superparamagnetic iron oxide nanoparticle leakage during low-frequency-ultrasound-induced blood-brain barrier opening in swine" Dec. 2011 *J Magn Reson Imaging*, 34(6):1313-1324.
Liu, "Magnetic resonance monitoring of focused ultrasound/magnetic nanoparticle targeting delivery of therapeutic agents to the brain" Aug. 2010 *Proc Natl Acad Sci U S A*, 107(34):15205-15210.
Liu, "Real-Time 2-D Temperature Imaging Using Ultrasound" Jan. 2010 *IEEE Trans Biomed Eng.*, 57(1):12-6.
Liu, "Three-dimensional image guidance for transcranial focused ultrasound therapy" Apr. 2017 IEEE 14th International Symposium on Biomedical Imaging (ISBI 2017), 916-919.
Liu, "Viscoelastic property measurement in thin tissue constructs using ultrasound" 2008 *IEEE Trans. Ultrason. Ferroelect. Freq. Contr.* 55(2):368-383.
Lockwood, "High-speed method for computing the exact solution for the pressure variations in the near field of a baffled piston" *The Journal of the Acoustical Society of America*, 53, No. 3, pp. 735-741:1973.
Lubinski, "Speckle tracking methods for ultrasonic elasticity imaging using short-time correlation" 1999 *IEEE Trans. UFFC.*, 46:82-96.
Luo, "Pulse wave imaging of normal and aneurysmal abdominal aortas in vivo" Apr. 2009 *IEEE Trans Med Imaging.*, 28(4):477-86.
Lynn, "Histology of cerebral lesions produced by focused ultrasound" 1944 *The American journal of pathology*, 20(3):637.
Maass-Moreno, "Noninvasive temperature estimation in tissue via ultrasound echo shifts. Part I. Theoretical model," 1996 *The Journal of the Acoustical Society of America*, 100(4.1):2514-2521.
Mahmoud, "In vivo vascular wall tissue characterization using a strain tensor measuring (STM) technique for flow-mediated vasodilation analyses" 2009 *Physics in Medicine and Biology*, 54(20):6217-6238.
Maimbourg, "3d printed adaptive acoustic lens as a disruptive technology for transcranial ultrasound therapy using single-element transducers" 2018 *Physics in Medicine & Biology*, 63(2):025026.
Manlapaz, "Effects of ultrasonic radiation in experimental focal epilepsy in the cat" 1964 *Experimental neurology*, 10(4):345-356.
Marquet, "Non-invasive transcranial ultrasound therapy based on a 3d ct scan: protocol validation and in vitro results" May 2009 *Phys Med Biol*, 54(9):2597-2613.
Martin, "High intensity focused ultrasound for noninvasive functional neurosurgery" 2009 *Annals of Neurology: Official Journal of the American Neurological Association and the Child Neurology Society*, 66(6):858-861.
Martin, "Investigation of HIFU produced emulsion for acoustic hemostasis," 2003 *Proc. 3rd Int. Symp. Ther. Ultrasound*, 1:351-356.
Marty, "Dynamic study of blood-brain barrier closure after its disruption using ultrasound: a quantitative analysis" Oct. 2012 *J Cereb Blood Flow Metab*, 32(10):1948-1958.
McDannold, "Transcranial magnetic resonance imaging-guided focused ultrasound surgery of brain tumors: initial findings in 3 patients" *Neurosurgery*, 66, No. 2, 323-332, 2010.
McGough, "Direct Computation of ultrasound phased-array driving signals from specified temperature distribution for hyperthermia," Aug. 1992 *IEEE Trans. Biomedical Engineering*, 39(8):825-835.
McGough, "Mode scanning: heating pattern synthesis with ultrasound phased arrays," 1994 *Int. Journal of Hyperthermia*, 10(3):433-442.
McGough, "Rapid calculations of time-harmonic nearfield pressures produced by rectangular pistons" *The Journal of the Acoustical Society of America*, 115, No. 5, pp. 1934-1941, 2004.
Mehic, "Increased anatomical specificity of neuromodulation via modulated focused ultrasound" 2014 *PLoS One*, 9(2):e86939.
Meyers, "Early experiences with ultrasonic irradiation of the pallidofugal and nigral complexes in hyperkinetic and hypertonic disorders" Jan. 1959 *J Neurosurg*, 16(1):32-54.

Miller, "Fundamental limitations of noninvasive temperature imaging by means of ultrasound echo strain estimation," 2002 *Ultrasound in Medicine and Biology*, 28(10):1319-1333.
Min, "Focused ultrasound-mediated suppression of chemically-induced acute epileptic EEG activity" 2011 *BMC Neurosci.*, 12:23.
Misaridis, "Use of modulated excitation signals in medical ultrasound. part I: basic concepts and expected benefits" Feb. 2005 *IEEE Trans. Ultrason., Ferroelect., Freq. Colltr.*, 52(2): 177-191.
Montaldo, "Spatio-temporal coding in complex media for optimum beamforming: the iterative time-reversal approach" Feb. 2005 *IEEE Trans. Ultrason., Ferroelect., Freq. Comr.*, 52(2):220-230.
Mougenot, "Automatic spatial and temporal temperature control for MR-guided focused ultrasound using fast 3D MR thermometry and multispiral trajectory of the focal point," Nov. 2004 *Magnetic Resonance in Medicine*, 52(5):1005-1015.
Mougenot, "Three-dimensional spatial and temporal temperature control with MR thermometry-guided focused ultrasound (mrghifu)," 2009 *Magnetic Resonance in Medicine*, 61:603-614.
Moyle, "Inlet conditions for image-based CFD models of the Carotid bifurcation: Is it reasonable to assume fully developed flow?" 2006 *Journ. of Biomechanical Engr. Transactions of the ASME*, 128(3):371-379.
Mucci, "A comparison of efficient beamforming algorithms" 1984 *IEEE Transactions on Acoustics, Speech, and Signal Processing*, 32(3):548-558.
Mueller, "Transcranial Focused Ultrasound Modulates Intrinsic and Evoked EEG Dynamics" 2014 *Brain Stimul.*, 7:900-908.
Naor, "Ultrasonic neuromodulation" 2016 *J. Neural Eng.*, 13:031003.
Nichols, *McDonald's Blood Flow in Arteries*, Hodder Arnold: New York, NY; 2005. Cover page, title page and table of contents.
Nightingale, "On the feasibility of remote palpation using acoustic radiation force," Jul. 2001 *J. Acoust. Soc. Amer.*, 110:625-634.
Ocheltree, "Sound field calculation for rectangular sources" 1989 *IEEE transactions on ultrasonics, ferroelectrics, and frequency control*, 36(2):242-248.
O'Donnell, "Coded excitation for synthetic aperture ultrasound imaging" Feb. 2005 *IEEE Trns. Ultrason., Ferroelect., Freq. Contr.*, 52(2):171-176.
Oppenheim et al., Discrete-time signal processing, Second Edition. Prentice-Hall, Upper Saddle River, New Jersey, 1999; 896 pages.
Patel, "Hard real-time closed-loop electrophysiology with the Real-Time experiment Interface (RTXI)" 2017 *PLoS Comput. Biol.*, 13:e1005430.
Paxinos, *"The mouse brain in sterotaxic coordinates"* 2004 Gulf Professional Publishing. Cover page, publisher page, table of contents.
Pernot, "High power density prototype for high precision transcranial therapy," 2003 *Proc. 3rd Int. Symp. Ther. Ultrasound*, 1:405-410.
Pernot, "Temperature estimation using ultrasonic spatial compounding," 2004 *IEEE Trans. Ultrason., Ferroelect., Freq. Contr.*, 51(5):606-615.
Pesavento, "A time efficient and accurate strain estimation concept for ultrasonic elastography using iterative phase zero estimation" 1999 *IEEE Trans. UFFC*, 46(5):1057-1067.
Pinton, "Direct phase projection and transcranial focusing of ultrasound for brain therapy" 2012 *IEEE Trans Ultrason Ferroelectr Freq Control*, 59(6):1149-59.
Podgorski, "Brain heating induced by near-infrared lasers during multiphoton microscopy" 2016 *J. Neurophysiol.* 116:1012-1023.
Poissonnier, "Control of prostate cancer by transrectal HIFU in 227 patients," 2007 *Eur. Urol.*, 51:381-387.
Prada, "Decomposition of the time reversal operator: Detection and selective focusing on two scatterers" 1996 *The Journal of the Acoustical Society of America*, 99(4):2067-2076.
Prada, "The iterative time reversal process: Analysis of the convergence," 1995 *J. Acoust. Soc. Amer.*, 95:62-71.
Pramanik, "Thermoacoustic and photoacoustic sensing of temperature," Sep. 2009 *Journal of Biomedical Optics*, 14(5): 054024.
Rabben, "An ultrasound-based method for determining pulse wave velocity in superficial arteries" 2004 *Journ. of Biomechanics*, 37(10):1615-1622.

(56) References Cited

OTHER PUBLICATIONS

Rabben, "Ultrasound-based vessel wall tracking: An autocorrelation technique with RF center frequency estimation" 2002 *Ultrasound in Medicine and Biology*, 28(4):507-517.
Raghupathy, "Generalized Anisotropic Inverse Mechanics for Soft Tissues" Aug. 2010 *J. Biomech. Eng.*, 132(8):081006.
Raymond, "Ultrasound enhanced delivery of molecular imaging and therapeutic agents in Alzheimer's disease mouse models" 2008 *PLoS One*, 3(5):e2175.
Revell et al., "Ultrasound Speckle Tracking for Strain Estimation," 2003 University of Bristol Department of Computer Science; Dec. 2003, 5 pgs.
Rezayat, "A Review on Brain Stimulation Using Low Intensity Focused Ultrasound" 2016 *Basic and Clinical Neuroscience*, 7 (3):187-94.
Ribbers, "Noninvasive two-dimensional strain imaging of arteries: Validation in phantoms and preliminary experience in carotid arteries in vivo" 2007 *Ultrasound in Medicine and Biology*, 33(4):530-540.
Rieke, "MR thermometry" 2008 *Journal of Magnetic Resonance Imaging: An Official Journal of the International Society for Magnetic Resonance in Medicine*, 27(2):376-390.
Rihaczek, "Radar waveform selection—a simplified approach" Nov. 1971 *IEEE Trans. Aerosp. Electron. Syst.*, AES-7(6):1078-1086.
Rohani, "Focused ultrasound for essential tremor: review of the evidence and discussion of current hurdles" *Tremor and Other Hyper-kinetic Movements*, 2017; 7. doi: 10.7916/D8Z89JN1.
Sakatani, "Somatosensory evoked potentials in rat cerebral cortex before and after middle cerebral artery occlusion" 1990 *Stroke* 21:124-132.
Salomir, "Hyperthermia by MR-guided focuses ultrasound: Accurate temperature control based on fast MRI and a physical model of local energy deposition and heat conduction," 2000 *Magnetic Resonance in Medicine*,43:342-347.
Salomir, "Image-based control of the magnetic resonance imaging guided focused ultrasound thermotherapy" 2006 *Topics in Magnetic Resonance Imaging*, 17(3):139-151.
Sanghvi, "Noninvasive surgery of prostate tissue by high-intensity focused ultrasound," Nov. 1996 *IEEE Trans. Ultrason., Ferroelectr., Freq. Contr.*, 43(6):1099-1110.
Sanghvi, "New developments in therapeutic ultrasound," Nov./Dec. 1996 *IEEE Eng. Med. Biol. Mag.*, 15(6):83-92.
Sapareto, "Thermal dose determination in cancer therapy," 1984 *Int. J. Rad. Onc. Biol. Phys.*, 10(6):787-800.
Sato, "Ultrasonic Neuromodulation Causes Widespread Cortical Activation via an Indirect Auditory Mechanism" 2018 *Neuron* 98:1031-1041.e5.
Savitzky, "Smoothing and differentiation of data by simplified least squares procedures." *Analytical chemistry*, 36, No. 8, pp. 1627-1639, 1964.
Sawyer, "Nanoparticle-based evaluation of blood-brain barrier leakage during the foreign body response" *Journal of Neural Engineering*, 10(2013) 016013; 10 pages.
Schiefer, "Moving forward: Advances in the treatment of movement disorders with deep brain stimulation" 2011 *Frontiers in Integrative Neuroscience*, 5:69.
Schoenhagen, "Coronary imaging: Angiography shows the stenosis, but IVUS, CT, and MRI show the plaque" 2003 *Cleveland Clinic Journ. of Medicine*, 70(8):713-719.
Seip, "Characterization of a Needle Hydrophone Array for Acoustic Feedback during Ultrasound Hyperthermia Treatments," 1992 *Ultrasonics Symposium Proceedings*, 2:1265-1269.
Seip, "Dynamic focusing in ultrasound hyperthermia treatments using implantable hydrophone arrays," Sep. 1994 *IEEE Trans. Ultrason., Ferroelectr., Freq. Control*, 41(5):706-713.
Seip, "High-intensity focused ultrasound (HIFU) phased arrays: Recent developments in transrectal transducers and driving electronics," 2003 *Proc. 3$^{rd}$ Int. Symp. Ther. Ultrasound*, 1:423-428.
Seip, "Invasive and Non-Invasive Feedback for Ultrasound Phased Array Thermotherapy," 1994 *Ultrasonics Symposium Proceedings*, 3:1821-1824.
Seip, "Non-Invasive Detection of Thermal Effects due to Highly Focused Ultrasonic Fields," 1993 *Ultrasonics Symposium Proceedings*, 2:1229-1232.
Seip, "Non-invasive estimation of tissue temperature response to heating fields using diagnostic ultrasound," 1995 *IEEE Trans. Biomed. Eng.*, 42(8):828-839.
Seip, "Noninvasive real-time multipoint temperature control for ultrasound phased array treatments," Nov. 1996 *IEEE Transactions on Ultrasonics Ferroelectrics and Frequency Control*, 43(6):1063-1073.
Seip, "Non-invasive Spatio-temporal Temperature Change Estimation Using Diagnostic Ultrasound," *Ultrasonics Symposium Proceedings*, 1995, pp. 1613-1616.
Shapoori, "An ultrasonic-adaptive beamforming method and its application for trans-skull imaging of certain types of head injuries; part i: Transmission mode" *IEEE Transactions on Biomedical Engineering*, 2015, 62(5):1253-1264.
Shehata, "Feasibility of targeting atherosclerotic plaques by high-intensity-focused ultrasound: an in vivo study" Dec. 2013 *J Vasc Interv Radiol*, 24(12):1880-1887.e2.
Shen, "New Coded-Excitation Ultrasound Imaging System—Part I: basic principles" 1996 *IEEE Trans. Ultrason., Ferroelect., Freq. Cont*, 43(1):131-140.
Shen, "A New Coded-Excitation Ultrasound Imaging System—Part II: Operator Design," 1996 *IEEE Trans. Ultrason., Ferroelect., Freq. Cont*, 43(1):141-148.
Shen, "An optimal image operator design technique for coded excitation ultrasound imaging system" *Ultrasonics Symposium Proceedings. IEEE*, 1994, 3:1777-1781.
Shen, "A Post-Beamforming Processing Technique for Enhancing Conventional Pulse-Echo Ultrasound Imaging Contrast Resolution," 1995 *IEEE Ultrasonics Symposium Proceedings*, pp. 1319-1322.
Shen, "On the design of a transversal filler bank for parallel processing multiple image lines in real-time acoustic imaging" in Acoustics, Speech, and Signal Processing, 1996. ICASSP-96. Conference Proceedings., IEEE International Conference, 6:3109-3112.
Shen, "Real-time 3d pulse-echo ultrasonic imaging with coded-excitation systems" in Image Processing, Oct. 1996. Proceedings. International Conference, 1:717-720.
Shen, "Filter-based coded-excitation system for high-speed ultrasonic imaging" Dec. 1998 *IEEE Transactions on Medical Imaging*, 17(6): 923-934.
Shung, "Scattering of ultrasound by blood" Nov. 1976 IEEE Trans Biomed Eng., 23(6):460-7.
Simon, "Combined ultrasound image guidance and therapy using a therapeutic phased array," May 1998 *SPIE Med. Imag.*, 3341:89-98.
Simon, "Estimation of Mean Scatterer Spacing Based on Autoregressive Spectral Analysis of Prefiltered Echo Data," 1995 *Ultrasonics Symposium Proceedings*, pp. 1153-1156.
Simon, "Two-Dimensional Temperature Estimation Using Diagnostic Ultrasound" Jul. 1998 *IEEE Transactions on Ultrasonics, Ferroelectrics, and Frequency Control*, 45(4):1088-1099.
Smith, "Control system for an MRI compatible intracavitary ultrasound array for thermal treatment of prostate disease," May-Jun. 2001 *International Journal of Hyperthermia*, 17(3):271-282.
Souchon, "Monitoring the formation of thermal lesions with heat-induces echo-strain imaging: a feasibility study," 2005 *Ultrasound in Medicine and Biology*, 31:251-259.
Souchon, "Ultrasonic elastography using sector scan imaging and a radial compression" 2002 *Ultrasonics*, 40(1-8):867-871.
Steidl, "Dual-mode ultrasound phased arrays for noninvasive surgery: Post-beamforming image compounding algorithms for enhanced visualization of thermal lesions," Jul. 2002 *Proc. IEEE Int. Symp. Biomed. Imag.*, 429-432.
Steinman, "Flow imaging and computing: large artery hemodynamics" Dec. 2005 *Annals of Biomedical Engineering*, 33(12):1704-1709.

(56) References Cited

OTHER PUBLICATIONS

Sumi, "Fine elasticity imaging utilizing the iterative rf-echo phase matching method" 1999 *IEEE Transactions on Ultrasonics, Ferroelectrics, and Frequency Control*, 46(1):158-166.
Sun, "Adaptive real-time closed-loop temperature control for ultrasound hyperthermia using magnetic resonance thermometry," Oct. 2005 *Concepts in Magnetic Resonance Part B—Magnetic Resonance Engineering*, 27B(1):51-63.
Sun, "Focusing of therapeutic ultrasound through a human skull: A numerical study," 1998 *J. Acoust. Soc. Amer.*, 104:1705-1715.
Swillens, "Two dimensional flow imaging in the carotid bifurcation using a combined speckle tracking and phase-shift estimator: a study based on ultrasound simulations and in vivo analysis" 2010 *Ultrasound in Medicine and Biology*, 36(10):1722-1735.
Swillens, "Two-dimensional blood velocity estimation with ultrasound: speckle tracking versus crossed-beam vector Doppler based on flow simulations in a carotid bifurcation model" 2010 *IEEE Transactions on Ultrasonics Ferroelectrics and Frequency Control*, 57(2):327-339.
Szabo, "Diagnostic ultrasound imaging: inside out," Elsevier Academic Press, Burlington, Massachusetts, 2004. Title page, copyright page, and table of contents, 12 pages total.
Tanaka, "Active circulators—the realization of circulators using transistors" 1965 *Proceedings of the IEEE*, 53:260-267.
Tanter, "Focusing and steering through absorbing and aberrating layers: Application to ultrasonic propagation through the skull," 1998 *J. Acoust. Soc. Amer.*, 103:2403-2410.
Taylor, "Open problems in computational vascular biomechanics: Memodynamics and arterial wall mechanics" Sep. 2009 *Comput Methods Appl Mech Eng.*, 198(45-46):3514-3523.
Tempany, "MR imaging-guided focuses ultrasound surgery of uterine leiomyomas: A feasibility study," Nov. 2003 *Radiology*, 226:897-905.
Ter Haar, "Therapeutic applications of ultrasound" 2007 *Prog. Biophys. Mol. Biol.*, 93:111-129.
Thomenius, "Evolution of ultrasound beamformers" 1996 *IEEE Ultrasonic Symposium Proceedings*, Nov. 1996, pp. 1615-1622.
Thomenius, "Recent Trends in Ultrasound Beamformation" Sep. 2005 IEEE Ultrasonics Symposium, Rotterdam, The Netherlands, 113 pages.
Trahey, "Angle independent ultrasonic blood flow detection by frame-to-frame correlation of B-mode images," *Ultrasonics*, Sep. 1988; 26(5):271-276.
Treat, "Improved anti-tumor effect of liposomal doxorubicin after targeted blood-brain barrier disruption by MRI-guided focused ultrasound in rat glioma" Oct. 2012 *Ultrasound Med Biol*, 38(10):1716-1725.
Treat, "Targeted delivery of doxorubicin to the rat brain at therapeutic levels using mri-guided focused ultrasound" Aug. 2007 *Int J Cancer*, 121(4):901-907.
Tsou, "Role of ultrasonic shear rate estimation errors in assessing inflammatory response and vascular risk" Jun. 2008 *Ultrasound Med Biol.*, 34(6): 963-972.
Tufail, "Transcranial pulsed ultrasound stimulates intact brain circuits" 2010 *Neuron* 66:681-694.
Tufail, "Ultrasonic neuromodulation by brain stimulation with transcranial ultrasound" Sep. 2011 *Nat Protoc*, 6(9):1453-1470.
Tung, "The mechanism of interaction between focused ultrasound and microbubbles in blood-brain barrier opening in mice" Nov. 2011 *J Acoust Soc Am*, 130(5):3059-3067.
Tutwiler, "Ultrasonic beamforming architectures" in Medical Imaging 1998: Ultrasonic Transducer Engineering, 3341, pp. 43-55, *International Society for Optics and Photonics*, 1998.
Tyler, "Noninvasive neuromodulation with ultrasound? A continuum mechanics hypothesis" Feb. 2011 *Neuroscientist*, 17(1):25-36.
Tyler, "Remote excitation of neuronal circuits using low-intensity, low-frequency ultrasound" Oct. 2008 *PLoS One*, 3(10):e3511. doi: 10.1371/journal.pone.0003511. Epub Oct. 29, 2008.
Uchida, "Transrectal high-intensity focused ultrasound for the treatment of localized prostate cancer: Eight-year experience," Nov. 2009 *Int. J. Urology*, 16(11):881-886.
Vanbaren, "2D Large Aperture Ultrasound Phased Arrays for Hyperthermia Cancer Therapy: Design, Fabrication, and Experimental Results," 1995 *Ultrasonics Symposium Proceedings*, pp. 1269-1272.
Vanbaren, "A new algorithm for dynamic focusing of phased-array hyperthermia applicators through tissue inhomogeneities," *IEEE Ultrasonics Symposium Proceedings*, 1993; 2:1221-1224.
Vanbaren, "Multi-Point Temperature Control During Hyperthermia Treatments: Theory and Simulation," Aug. 1995 *IEEE Transactions on Biomedical Engineering*, 41(5):706-713.
Vanbaren, "Real-time Dynamic Focusing through Tissue Inhomogeneities during Hyperthermia Treatments with Phased Arrays," 1994 *Ultrasonics Symposium Proceedings*, 3:1815-1819.
Vanne, "MRI feedback temperature control for focused ultrasound surgery," 2003 *Physics in Medicine and Biology*, 48(1):31.
Varghese, "Direct strain estimation in elastography using spectral cross-correlation" 2000 *Ultrasound in Med. Biol.*, 26(9):1525-1537.
Vyas, "Extension of the angular spectrum method to calculate pressure from a spherically curved acoustic source" Nov. 2011 *J Acoust Soc Am.*, 130:2687-93.
Wagner, "Fundamental correlation lengths of coherent speckle in medical ultrasonic images" Jan. 1988 IEEE *Tmns. Ultrason., Ferroelect., Freq. Contr.*, 35(1):34-44.
Wan, "A 2d post-beamforming filter for contrast restoration in medical ultrasound: in vivo results" 2009 *Conf. Proc IEEE Eng Med Biol Soc*, 2009:1945-8.
Wan, "A Post-Beamforming 2-D Pseudoinverse Filter for Coarsely Sampled Ultrasound Arrays" Sep. 2009 *IEEE Trans Ultrason Ferroelectr Freq Control.*, 56(9):1888-1902.
Wan, "Imaging with concave large-aperture therapeutic ultrasound arrays using conventional synthetic-aperture beamforming" Aug. 2008 *IEEE Trans Ultrason Ferroelectr Freq Control*, 55(8):1705-18.
Wan, "Imaging vascular mechanics using ultrasound: Phantom and in vivo results" Apr. 14-17, 2010, 7th IEEE International Symposium on Biomedical Imaging: From Nano to Macro, ISBI 2010, Rotterdam; Netherlands, Article No. 5490152, 980-983.
Wan, "Simultaneous imaging of tissue motion and flow velocity using 2D phase-coupled speckle tracking" 2010 *Proceedings—IEEE Ultrasonics Symposium*, 2010:487-400.
Wan, "Ultrasound surgery: Comparison of strategies using phased array systems," Nov. 1996 *IEEE Trans. UFFC*, 43(6):1085-1008.
Wang, "Adaptive 2-D Cylindrical Section Phased Array System for Ultrasonic Hyperthermia," 1992 *Ultrasonics Symposium Proceedings*, 2:1261-1264.
Wang, "Effects of phase quantization errors on field patterns generated by an ultrasound phased array hyperthermia applicator," 1991 *IEEE Trans. Ultrasonics Ferroelec. Frequency Control*, 38(5): 521-531.
Wang, "Phase aberration correction and motion compensation for ultrasonic hyperthermia phased arrays: Experimental results" 1994 *IEEE Trans. on Ultrason., Ferroelec., and Freq. Control*, 41(l):34-43.
Weintraub, "The emerging role of transcranial magnetic resonance imaging-guided focused ultrasound in functional neurosurgery" 2016 *Movement Disorders*, 32(1):20-27.
Weitzel, "High-Resolution Ultrasound Elasticity Imaging to Evaluate Dialysis Fistula Stenosis" Jan. 2000 *Seminars in Dialysis*, 22(1):84-80.
White, "Effect of the skull in degrading the display of echoencephalographic b and c scans" *The Journal of the Acoustical Society of America*, 44, No. 5, pp. 1339-1345, 1968.
White, "The deformation of the ultrasonic field in passage across the living and cadaver head" *Medical and biological engineering*, 7, No. 6, pp. 607-618, 1969.
White, "Transcranial ultrasound focus reconstruction with phase and amplitude correction" 2005 *IEEE Trans. Ultrason. Ferroelectr. Freq. Control*, 52:1518-1522.
Wright, "Ultrasonic stimulation of peripheral nervous tissue: an investigation into mechanisms" 2015 *J. Phys. Conf. Ser.*, 581:012003.

(56) References Cited

OTHER PUBLICATIONS

Wu, "Advanced hepatocellular carcinoma: Treatment with high-intensity focused ultrasound ablation combined with transcatheter arterial embolization," *Radiology*, May 2005; 235(2):659-667.
Wu, "Feasibility of US-guided high-intensity focused ultrasound treatment in patients with advanced pancreatic cancer: Initial experience," *Radiology*, Sep. 2005; 236(3):1034-1040.
Wu, "Time reversal of ultrasonic fields. II. Experimental results," *IEEE Trans. Ultrason., Ferroelectr., Freq. Control*, Sep. 1992; 39(5):567-578.
Wulff, "Effects of ultrasonic vibrations on nerve tissues." *Proceedings of the Society for Experimental Biology and Medicine*, 1951, 76(2):361-366.
Yang, "Neuromodulation of sensory networks in monkey brain by focused ultrasound with MRI guidance and detection" 2018 *Sci. Rep.* 8:7993.
Yang, "Transcranial Ultrasound Stimulation: A Possible Therapeutic Approach to Epilepsy" 2011 *Medical Hypotheses* 76(3):381-83.
Yao, "Dual-mode ultrasound phased arrays for imaging and therapy," Apr. 2004 *Proc. IEEE Int. Symp. Biomed. Imag.*, 1:25-28.
Yao, "Enhanced lesion visualization in image-guided noninvasive surgery with ultrasound phased arrays," Oct. 2001 *Proc. 23$^{rd}$ Annu. Int. Conf. IEEE Eng, Med. Biol. Soc.*, 3:2492-2495.
Yao, "Real-time monitoring of the transients of HIFU-induced lesions," Oct. 2003 *Proc. IEEE Ultrason. Symp.*, 1:1006-1009.
Ye, "Frequency Dependence of Ultrasound Neurostimulation in the Mouse Brain" 2016 *Ultrasound Med Biol.*, 42(7):1512-30.
Yin, "A numerical study of transcranial focused ultrasound beam propagation at low frequency" Apr. 2005 *Phys Med Biol*, 50(8):1821-1836.
Yoo, "Focused ultrasound modulates region-specific brain activity" 2011 *NeuroImage*, 56:1267-1275.
Yoshino, "Effects of focused ultrasound sonodynamic treatment on the rat blood-brain barrier" Mar. 2009 *Anticancer Res*, 29(3):889-895.
Younan, "Influence of the pressure field distribution in transcranial ultrasonic neurostimulation" Aug. 2013 *Med Phys*, 40(8):082902.
Yuh, "Delivery of systemic chemotherapeutic agent to tumors by using focused ultrasound: Study in a murine model," Feb. 2005; *Radiology*, 234(2):431-437.
Zhang, "Defining the optimal age for focal lesioning in a rat model of transcranial hifu" Feb. 2015 *Ultrasound Med Biol*, 41(2):449-455.
European Search Report dated Jul. 27, 2020 for European Patent Application No. 20176810.8, 8 pages.
English translation of Office Action for Chinese Patent Application No. 201810722985.7, dated Nov. 24, 2020, 15 pages.
Trahey, Gregg E., John W. Allison, and OlafT. Von Ramm. "Angle independent ultrasonic detection of blood flow." IEEE Transactions on Biomedical Engineering 12 (1987): 965-967.

\* cited by examiner

| Algorithm 1 Optimization of the DMUA Excitation Vector |
|---|
| 1: procedure SOLVE OPTIMIZATION PROBLEM($H_T^{(i)}, H_C^{(i)}, p_T, u_{opt}^{(i)}$) |
| 2: $\quad H_T = H_T^{(i)}, H_C = H_C^{(i)}$ |
| 3: $\quad W_T = H_T^H H_T, W_C = \left(H_C^H H_C + \gamma_C I\right), \gamma_C > 0$ can be obtained using *Lagrange multipliers* or *singular value decomposition* of $H_C$ |
| 4: $\quad$ Lagrange (MNLS): |
| $$u_{opt}^{(i)} = W_C^{-1} H_T^H \left(H_T W_C^{-1} H_T^H\right)^\dagger p_T$$ |
| 5: end procedure |

FIG. 7

WEARABLE TRANSCRANIAL DUAL-MODE ULTRASOUND TRANSDUCERS FOR NEUROMODULATION

CROSS-REFERENCE TO RELATED APPLICATIONS

The present application claims the benefit of U.S. Provisional Application Ser. No. 62/653,873, filed Apr. 6, 2018, which is incorporated by reference.

STATEMENT REGARDING FEDERALLY SPONSORED RESEARCH OR DEVELOPMENT

This invention was made with government support under NS098781 and NS087887 awarded by the National Institutes of Health. The government has certain rights in the invention.

BACKGROUND

The present disclosure relates to ultrasound transducer systems. In particular, the present disclosure relates to ultrasound transducer systems for imaging and therapy.

Transcranial focused ultrasound (tFUS) for neuroscience and neurosurgery has potential as a therapeutic modality for numerous neurologic and psychiatric conditions including epilepsy, depression, anxiety disorders, movement disorders, and traumatic brain injury.

Treatment of some conditions requires invasive surgery to implant a medical device for deep brain stimulation (DBS) therapy. For example, epilepsy may be treated using surgical intervention, which may be considered the best option for patients who do not respond to more than one drug treatment. However, surgery referral times can be long for many patients, particularly those who have suffered from many years of seizures. Without removing the skull, tFUS has been guided by magnetic resonance (MR) due to its high soft-tissue contrast and specificity to a variety of lesions and abnormalities in the brain. However, in using MR, obtaining high-specificity feedback regarding the tFUS-tissue interactions remains difficult, especially when short bursts of sub-therapeutic tFUS are used, which may hinder understanding what therapeutic endpoints can be achieved using tFUS.

Subtherapeutic tFUS has been used with a single-frequency continuous waveform (CW) for neuromodulation and a carrier frequency that is conservatively low. Using a low carrier frequency may minimize the severe aberrations and attenuation through the skull. However, lowering the frequency of tFUS may increase the size of the focal spot, especially in the axial direction, and may increase the probability of forming potentially harmful interference patterns.

Dual-mode ultrasound array (DMUA) applicators may provide thermal and non-thermal tFUS neuromodulation with a high degree of spatiotemporal precision. However, many tFUS DMUA applicators are too bulky for use in freely-moving patients, which may make use of such applicators outside of a clinical setting impractical.

SUMMARY

The techniques of this disclosure relate to the design and fabrication of next-generation DMUA tFUS applicators, which can be used to provide therapy similar to deep brain stimulation (DBS) without being invasive. Further, techniques of the present disclosure may provide the full benefits of the DMUA approach in monitoring and delivery of tFUS imaging or therapy to mobile and fully awake subjects (e.g., animals and humans).

Various aspects of the present disclosure relate to employing light-weight, conformable (e.g., sufficiently flexible), and wearable patches of ultrasound transducers for delivery, monitoring, and spatiotemporal control of localized tFUS. Various aspects of the present disclosure relate to full-duplex transmit-receive circuitry for transcranial neuromodulation, which may be used for continuous monitoring of tFUS application.

In one aspect, the present disclosure provides an ultrasound transducer system including an ultrasound transducer configured to provide a transmit ultrasound wavefront in response to an excitation waveform and to provide a reflection waveform in response to a reflected ultrasound wavefront. The ultrasound transducer system also includes a circulator operably coupled to the ultrasound transducer. The circulator includes a first port configured to receive an excitation waveform from a transmit circuit. The circulator also includes a second port configured to: provide the excitation waveform to the ultrasound transducer to provide a transmit ultrasound wavefront and receive a reflection waveform from the ultrasound transducer corresponding to a reflection of the transmit ultrasound wavefront during or after providing the excitation waveform. The circulator further includes a third port configured to provide the reflection waveform to a receive circuit during or after receiving the excitation waveform from the transmit circuit.

In another aspect, the present disclosure provides an ultrasound transducer system including a lens layer configured to partially or completely compensate for a predetermined ultrasound beam distortion associated with an ultrasound obstacle. The ultrasound transducer system also includes an ultrasound transducer layer configured to deliver a transmit ultrasound wavefront into the lens layer and to receive a reflected ultrasound wavefront that has passed through the lens layer corresponding to a reflection of the transmit ultrasound wavefront. The ultrasound transducer system further includes a coarse aperture layer coupled to the ultrasound transducer layer and comprising a plurality of channel conductors. Each channel conductor is operably coupled to a different portion of a surface of the ultrasound transducer layer. Each channel conductor defines a conductive surface area having a size or shape different than at least one other channel conductor. Further, the ultrasound transducer system includes a backing layer comprising an electrically insulative material coupled to the coarse aperture layer.

In another aspect, the present disclosure provides a method for generating an aperture having a reduced number of sampling elements. The method includes generating a fine aperture having a plurality of sampling elements each corresponding to a different region of an ultrasound transducer surface. The method also includes determining at least one propagation operator based on the fine aperture and at least one target point. The method further includes determining an excitation waveform vector based on the at least one propagation operator. The elements of the excitation waveform vector correspond to the sampling elements. Also, the method includes clustering sampling elements of the fine aperture into groups of two or more sampling elements based on similar narrowband excitation waveforms in the excitation waveform vector. Further, the method includes generating a coarse aperture with the clustered sampling elements.

BRIEF DESCRIPTION OF THE DRAWINGS

The disclosure may be more completely understood in consideration of the following detailed description of various embodiments of the disclosure in connection with the accompanying drawings.

FIG. 7 is pseudocode of an iterative algorithm that may be used to provide optimal sampling elements for an aperture for use with, e.g., the systems of FIGS. 1-3.

DETAILED DESCRIPTION

Figure 1:
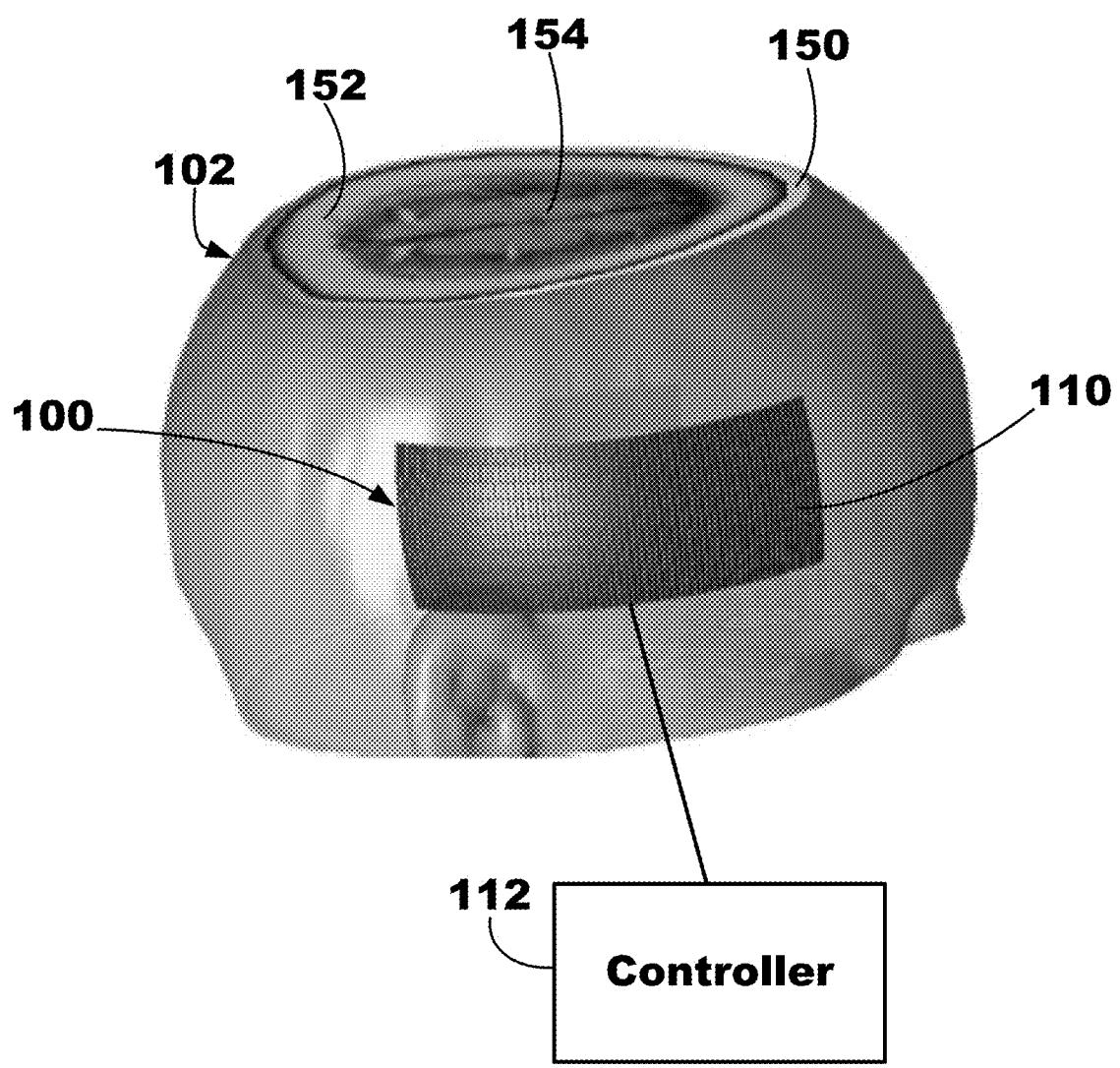
FIG. 1 is an illustration of an ultrasound transducer system including a patch for tFUS neuromodulation. In the illustration, a 3 D-printed lens is attached to the scalp with appropriate adhesive material.

The present application relates to a wearable transcranial dual-mode ultrasound transducer system for imaging or therapy and, in particular, to a wearable transcranial dual-mode ultrasound transducer system for imaging or therapy. Although reference is made herein to patient therapy, the ultrasound transducer device and system may be used for any suitable application, such as using ultrasound in research or non-medical settings. Various other applications will become apparent to one of skill in the art having the benefit of the present disclosure.

Transcranial focused ultrasound (tFUS) offers the potential of precise spatial and temporal control of neural activity with a wide range of applications in the treatment of brain conditions and neurological disorders. tFUS neuromodulation systems described herein may employ light-weight, wearable patch transducers for the spatiotemporal control of tFUS in human patients, awake rodents, and/or roaming large animals. The envisioned system may be used to deliver controlled spatiotemporal tFUS energy as a prescription in order to maximize the treatment efficacy at the target while minimizing collateral inhibition/stimulations at other locations within the treatment volume.

Transcranial focused ultrasound (tFUS) may be used as a treatment modality for a range of brain conditions and neurological disorders. Compared to well established neuromodulation methods, tFUS may be used to produce spatially precise neural inhibition/stimulation while being non-invasive. Furthermore, tFUS appears to be non-disease specific, which means it has the potential to be used in a wide range of treatments. Several potential advantages of dual-mode ultrasound array (DMUA) technology may benefit from guidance, monitoring, and delivery of tFUS in vivo.

The ultrasound transducer devices and systems described herein may provide continuous delivery, monitoring, and control of localized tFUS using light-weight, conformable structures. The ultrasound transducer system may employ light-weight, conformal array elements with supporting front-end electronics and real-time signal processing capabilities for the delivery of tFUS energy with continuous monitoring. For example, a light-weight polymer transducer material may be used to implement a wideband ultrasound transducer array with appropriate backing to maintain low-profile patch-like tFUS applicators. Patch-like ultrasound transducer applicators may be suitable for long-term application in research subjects and human patients. tFUS neuromodulation arrays may be custom-designed or fitted for each patient based on the target voxel(s) and the optimal access window(s) through the skull.

The DMUA may utilize the same array elements for delivering the tFUS neuromodulation (or therapy) and imaging the mechanical and/or thermal tissue response with high spatial and temporal resolutions. To improve the DMUA's ability to characterize the tissue response to tFUS, front-end electronic circuitry may be configured to allow full-duplex transmit-receive operation. This may provide a powerful tool for the detection and localization of low levels of inertial cavitation that may be responsible for the observed neural inhibition/stimulation effects of non-thermal tFUS beams. This tool may also allow for the use of transmit waveforms with very large time-bandwidth product, which could improve the spatial localization of ultrasound neuromodulation with continuous monitoring of acoustic bioeffects.

It may be beneficial to provide an ultrasound transducer device and system to facilitate delivering therapy in a minimally invasive or non-invasive manner. It may further be beneficial to facilitate the low intensity, high focus application of ultrasound to specific target volumes in a patient's tissue, which may reduce undesirable interference and side effects. It may also be beneficial to provide a device and system that facilitates portable use with a patient to receive therapy outside of a clinical setting, preferably without significantly impairing normal daily activities.

In some embodiments, the present disclosure provides an innovative design of front-end electronics for DMUA transducers employing full-duplex transmit-receive operation to allow monitoring of acoustic feedback simultaneously with the application of neuromodulation. This may be used in the detection and localization of subtle inertial cavitation activities associated with tFUS neuromodulation. Further, the use of wideband tFUS waveforms with high time-bandwidth product can achieve unprecedented levels of localization of neuromodulation effects.

In some embodiments, the present disclosure provides the use of three-dimensional (3D) ultrasound imaging of the subject's skull/scalp to design and construct custom-fit, light-weight DMUA tFUS applicators for use in awake rodents or freely-moving patients. These applicators may impact the clinical use of tFUS technology and may also impact the value of animal research when used for the application and monitoring of tFUS on awake rodents and freely-moving large animals. These applicators may use innovations in transducer design and fabrication, mixed analog-digital electronics, and real-time array signal processing.

As used herein, the term "transducer element" refers to a single transducer or a portion of a transducer layer configured to act as a single transducer. For example, a portion of a transducer layer may be operably coupled to a channel conductor and act as one transducer element. The portion of the transducer layer may also be referred to as a sampling element of an aperture.

As used herein, the term "excitation vector" refers to a representation of ultrasound energy including a plurality of vector elements, each representing ultrasound energy to be delivered by one transducer element. In particular, each element of an excitation vector may represent (e.g., contain or correspond to) the magnitude and phase of a narrowband waveform representing ultrasound energy.

As used herein, the term "waveform" refers to signals provided to and from a transducer element. Each waveform may include one or more frequencies in an overall bandwidth of the transducer element. In general, one excitation waveform may be determined for each transducer element and may be a broadband arbitrary waveform.

As used herein, "voxel" refers to an element of volume in an array of discrete elements of volume that constitute a three-dimensional space (e.g., used to represent a target volume of tissue).

Reference will now be made to the drawings, which depict one or more aspects described in this disclosure. However, it will be understood that other aspects not depicted in the drawings fall within the scope of this disclosure. Like numbers used in the figures refer to like components, steps and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 is a perspective view of one ultrasound transducer system 100. Ultrasound transducer system 100 may be modular and include patch 110, or transducer portion, which is shown attached to subject 102 (e.g., a patient). As illustrated, patch 110 is coupled adjacent to surface layer 150 (e.g., skin/scalp) of the head of subject 102. The ultrasound transducer system 100 may include controller 112 (e.g., a control circuit or circuitry) operably coupled to patch 110. A cross-section of head 102 is shown for illustrative purposes, in particular, to show the subject's ultrasound obstacle 152 (e.g., a skull, which may cause ultrasound distortion) and subject tissue 154 (e.g., brain tissue).

System 100 may be configured to provide continuous delivery, monitoring, and control of localized tFUS and may use a light-weight, conformable transducer array. Further, system 100 configured as an ultrasound patch may be used to provide a personalized-medicine approach to tFUS neuromodulation. Light-weight, custom-designed arrays may be included in patch 110 and optimized for targeting specific circuit(s) within the brain utilizing low-power drivers and processors, which may be included in controller 112, for closed-loop control of neuromodulation. Patch 110 may be described as a dual-mode ultrasound array (DMUA) applicator.

Transducer system 100 may be described as a tFUS applicator and may be customized to each subject to optimize ultrasound energy deposition in a small target volume (e.g., at target points in a target volume). The subject-specific customization may facilitate a dramatic reduction in the number of array elements needed to provide effective ultrasound energy deposition in the small target volume.

In some embodiments, controller 112 includes front-end circuitry that may be used for full-duplex DMUA operation, which may improve detection and localization of subtle cavitation activity while tFUS neuromodulation is active. The front-end circuitry may also be used for transmitting waveforms with very large time-bandwidth product (e.g., large bandwidth and/or long duration), which may also have appropriate, or desirable, correlation properties (e.g., orthogonal or almost orthogonal waveforms) for improved spatial localization in the axial direction (e.g., a direction orthogonal to a transducer major surface or substantially parallel to the direction of propagation of the transmit ultrasound wavefront).

Figure 2:
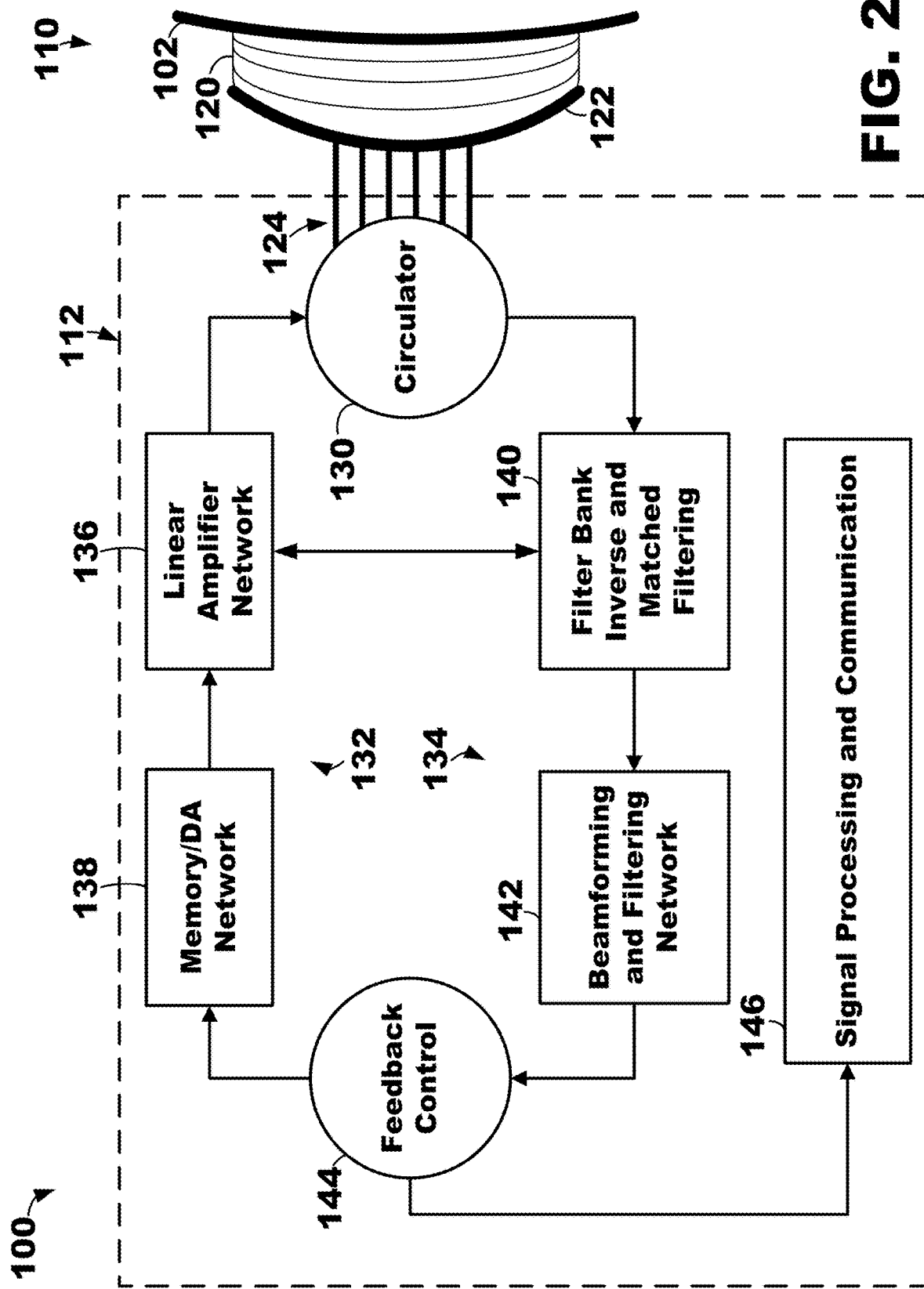
FIG. 2 is a schematic illustration showing the ultrasound transducer system of FIG. 1 showing the patch and controller.

FIG. 2 is a schematic illustration showing ultrasound transducer system 100 including patch 110 and controller 112 (e.g., control circuit). As illustrated, patch 110 may include lens 120 positioned between transducer 122 (e.g., transducer array of one or more elements) and the subject 102. Patch 110 may be operably coupled to controller 112 using one or more connectors 124. In general, the lower number of connectors 124, the smaller the patch 110 and overall system 100 can be. Each connector 124 may include a wired connection. In some embodiments, each connector 124 includes one or more conductors extending between patch 110 and controller 112 to provide an electrical connection.

Each connector 124 may be associated with a channel of the system 100. As used herein the term "channel" refers to circuitry and/or operative couplings that enable controller 112 to generate one or more ultrasound wavefronts with patch 110 using one or more ultrasound waveforms.

Controller 112 may be contained within a portable package to provide a portable control circuit for system 100. In particular, a portable configuration of controller 112 may be useful for a low channel-count configuration of system 100, which can be used for low intensity imaging or therapy outside of a clinical setting (e.g., on the move). In some cases, controller 112 may be contained within a larger, stationary package, which may be used to provide a robust control circuit for system 100. In particular, a robust configuration of controller 112 may be useful for a high channel-count configuration of system 100, which can be used, for example, in a clinical setting, for low or high intensity imaging or therapy or to configure a portable controller to be used outside of the clinic.

Using the high channel-count configuration may be appropriate for designing laboratory or even clinical DMUAs for arbitrary targeting within the brain cavity, e.g., targeting a region within the hippocampus in one application versus the thalamus in another using the same DMUA. The overall system 100 may be bulky, requiring relatively large coupling medium (e.g., usually a water bolus) and cabling for relatively large number of elements. The high-channel count configuration may not be feasible for use in scenarios where the subject is awake and able to perform some tasks while tFUS neuromodulation is being applied.

Using the low channel-count configuration may be more appropriate for awake and mobile subjects. In some embodiments, the low channel-count configuration may be used for delivery of modulated tFUS beams to one or more discrete voxels in a target volume (e.g., fewer target voxels or target points in a smaller volume).

Controller 112 may include one or more components (e.g., processing circuits or circuitry) configured to use the patch 110 to provide imaging of, or therapy to, head 102 of the patient. As illustrated, controller 112 may include circulator 130. Circulator 130 may be operably coupled to transmit circuit 132 and receive circuit 134. Circulator 130 may facilitate the ability of the system 100 to provide full-duplex transmit-receive functionality. In addition, or alternatively, certain transducer elements may be selected and dispersed within the DMUA structure of patch 110 with dedicated receive-only circuitry for the detection of subtle cavitation activity.

In general, a higher signal-to-noise ratio (SNR) for receive circuitry of controller 112 is desirable (e.g., maximizing the SNR of the receiver), which may depend on the performance of circulator 130. Receive circuitry may be described as including circulator 130 and receive circuit 134. In some embodiments, field-programmable gate array (FPGA) circuitry with programmable amplifier networks may be used in the receive circuitry to achieve a high SNR.

Transmit circuit 132 may include memory and digital-to-analog (DA) network 138 and linear amplifier network 136. Linear amplifier network 136 may include broadband matching network configured to optimize the efficiency of the transmission through circulator 130 and transducer 122. Memory and DA network 138 may be configured to store the element waveforms necessary to produce a desired wavefront near the target point(s) while avoiding direct exposure to any critical point(s) defined by the user.

Receive circuit 134 may include filter bank inverse and matched filtering network 140 and beamforming and filtering network 142. Filter bank inverse and matched filtering network 140 may be configured to correct for waveform distortion due to propagation in inhomogeneous media (e.g., skull). Beamforming and filtering network 142 may be configured to maximize the SNR from the target point(s) and suppress interference from strongly scattering objects. In some embodiments, linear amplifier network 136 may be operably coupled to filter bank inverse and matched filtering network 140 to produce synchronized transmission wavefronts for motion tracking, elastography, thermography, and/or other signal processing.

Both transmit circuit 132 and receive circuit 134 may be operably coupled to feedback control 144. Feedback control 144 may be configured to facilitate using different modes of the system, such as adaptive imaging mode and therapy mode.

Feedback control 144 may be operably coupled to signal processing and communication processor 146. Signal processing and communication processor 146 may be configured to produce sensing and imaging data and, for example, transmit wirelessly to a mobile device. In particular, signal processing and communication processor 146 may be configured to interpret a reflection waveform from receive circuit 134 for storage or processing.

In some embodiments, patch 110 may be described as a structure including "super" elements that connect to a full transducer element array (e.g., a high channel-count controller 112 ). An algorithm may be used to calibrate and/or design a printed circuit board defining the "super" array elements. The "super" array elements may be irregularly shaped (e.g., have an irregularly shaped area). As used herein with respect to array elements, the term "irregular" may refer to non-uniformly shaped elements in an array (e.g., two or more elements having different shapes) or non-standard shapes (e.g., one or more elements having non-circular or non-rectangular shapes). The system 100 may be described as a reconfigurable ultrasound system that includes patch 110, which can be connected to different circuitry interfaces (e.g., a fully capable clinical interface and a portable interface with "super" array elements when used as a wearable device). Transmitting long duration waveforms (e.g., long pulse duration or continuous waveforms) may be used to provide high focusing gain while maintaining low intensity outside the target volume, which may be facilitated by using circulators 130.

One or more of the components, such as controllers, circuits, or circuitry, described herein may include a processor, such as a central processing unit (CPU), computer, logic array, or other device capable of directing data coming into or out of system 100. The controller may include one or more computing devices having memory, processing, and communication hardware. The controller may include circuitry used to couple various components of the controller together or with other components operably coupled to the controller.

The functions of the controller may be performed by hardware and/or as computer instructions on a non-transient computer readable storage medium. The processor of the controller may include any one or more of a microprocessor, a microcontroller, a digital signal processor (DSP), an application specific integrated circuit (ASIC), an FPGA, and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

Figure 3:
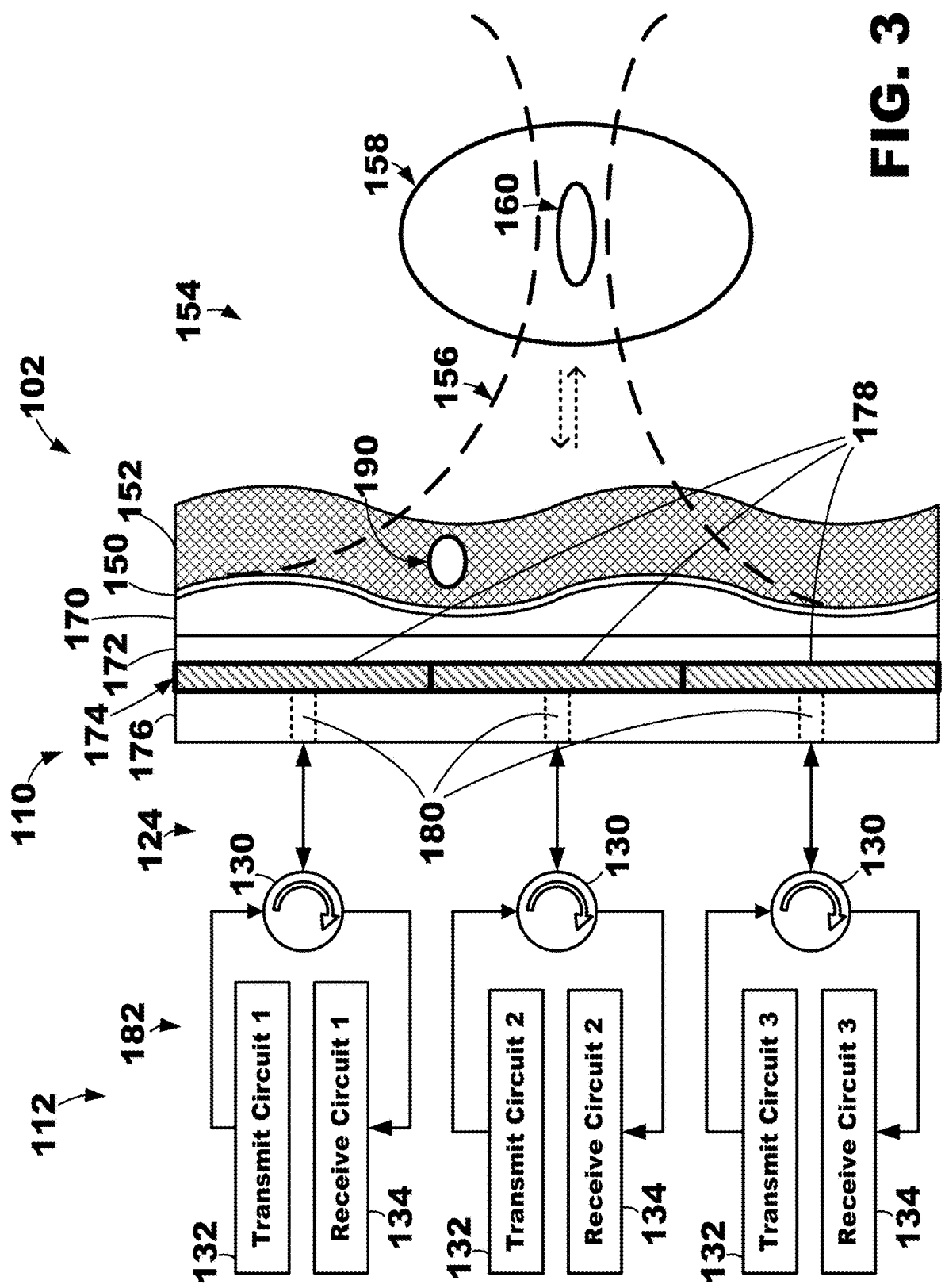
FIG. 3 is a schematic illustration showing the controller of FIGS. 1-2 operably coupled to the patch using connectors.

FIG. 3 is a schematic illustration showing a controller 112 (e.g., control circuit) operably coupled to patch 110 using connectors 124 with the patch being attached to subject 102. Different regions may be defined relative to subject 102. In particular, patch 110 may be coupled to surface layer 150 (e.g., skin or scalp) of subject 102. Ultrasound obstacle 152 (e.g., skull) typically separates skin, or surface layer, 150 from subject tissue 154 (e.g., brain tissue). Patch 110 (e.g., a tFUS neuromodulation array) may be custom-designed or fitted for each patient based on the target voxel(s) and the optimal access window(s) through the skull (e.g., obstacle 152).

Patch 110 is configured to deliver ultrasound energy to patient through surface layer 150, obstacle 152, and tissue 154 accord8ing to an ultrasound field of view (FOV) 156 (e.g., ultrasound imaging field of view, or IxFoV). In general, FOV 156 is configured to direct one or more ultrasound transmit wavefronts from patch 110 toward target volume 158 (e.g., therapeutic operating field, or ThxOF). The number of channels and the size of the target volume 158 may be related (e.g., larger target volumes may use higher numbers of channels to achieve desired focusing gains). For example, target volume 158 may have a width or diameter up to 10 mm for a controller 112 having up to 10 channels.

Target volume 158 may include one or more target voxels 160 (e.g., target points). Target voxel 160 may reflect ultrasound energy from patch 110 back to the patch to be detected as an ultrasound reflection wavefront. In general, target voxel 160 may be described as a volume, or point, where it is desirable to deposit ultrasound energy. In other words, it may be desirable to have high or maximal focusing gain at target voxels 160.

Obstacle 152 may include one or more critical voxels 190 (e.g., critical points). As used herein, the term "critical voxel" refers to a volume, or point, where it is desirable to avoid depositing ultrasound energy. It may be desirable to have low or minimal focusing gain at critical voxels 190. The term "critical" is not intended to convey that it is necessary for the operation of patch 110.

Patch 110 may include one or more ultrasound lens layer 170, ultrasound transducer layer 172 (e.g., including one or more transducers), ultrasound aperture layer 174, and backing layer 176. Lens layer 170 may be positioned adjacent to surface layer 150 and configured to partially or completely compensate for a predetermined ultrasound beam distortion associated with obstacle 152 (e.g., based on a determined propagation operator corresponding to the obstacle). Lens layer 170 may be coupled to transducer layer 172. Lens layer 170 may be positioned to receive a transmit ultrasound wavefront from transducer layer 172.

A site-specific acoustic lens layer 170 that conforms to the skull/scalp geometry in the access region may be formed, for example, using various methods of 3D printing. In some embodiments, three-dimensional (3D) image data of a skull/scalp (e.g., obstacle 152/ surface layer 150) may be used to design an acoustic lens to cover a predetermined aperture (e.g., a coarse or fine aperture). In particular, the lens geometry may be derived from the rendered 3D surface of the skull intersecting with the DMUA tFUS beam.

A non-limiting example of material that may be used to form lens layer 170 includes FLGPLC02, a photopolymer resin used in 3D printing, or any other suitable glass-like material. FLGPLC02 has acoustic properties similar to glass and may be used to provide a low-loss coupling medium, for example, as described in W. Chan, T. Hies, and C.-D. Ohl, *Laser-generated focused ultrasound for arbitrary waveforms*, Appl. Phys. Lett., 109:174102, 2016. A glass-like material may be used to implement phase-conjugate acoustic lenses, for example, as described in R. Lalonde and J. W. Hunt, *Variable frequency field conjugate lenses for ultrasound hyperthermia*, IEEE Transactions on Ultrasonics, Ferroelectrics, and Frequency Control, 42(5):825-831, September 1995, and R. J. Lalonde, A. Worthington, and J. W. Hunt, *Field conjugate acoustic lenses for ultrasound hyperthermia*, IEEE Transactions on Ultrasonics, Ferroelectrics, and Frequency Control, 40(5):592-602, September 1993.

A phase-conjugate acoustic lens layer 170 may be formed using a pseudoinverse pattern synthesis method, for example, as described in E S Ebbini and C A Cain, *Multiple-focus ultrasound phased array pattern synthesis—Optimal driving signal distributions for hyperthermia*, IEEE TRANSACTIONS ON ULTRASONICS FERROELECTRICS AND FREQUENCY CONTROL, 36(5):540-548, September 1989.

Transducer layer 172 may receive an excitation waveform through the ultrasound aperture layer 174 and produce a transmit ultrasound wavefront in response to, or based on, the excitation waveform. For example, transducer layer 172 may be configured to deliver a transmit ultrasound wavefront into lens layer 170 based on the excitation waveform. Transducer layer 172 may be configured to provide a reflection waveform to the ultrasound aperture layer 174 in response to receiving a reflected ultrasound wavefront. For example, transducer layer 172 may receive a reflected ultrasound wavefront that has passed through lens layer 170 corresponding to a reflection of the transmit ultrasound wavefront.

Transducer layer 172 may be formed from any suitable material for generating ultrasound wavefronts in response to receiving an excitation waveform. Lightweight polymer transducer material may be used to implement wideband a DMUA with appropriate backing to maintain a low-profile patch-like tFUS applicator. The transducer layer 172 may include polyvinylidene fluoride (PVDF) material. In some embodiments, transducer layer 172 is formed of a PVDF piezoelectric and may have a 9-micron to 25-micron thickness. PVDF transducers for transducer layer 172 may be designed and fabricated to have low-profiles. MR-compatible, low-profile, high-power PVDF transducers may be designed and fabricated as disposable HIFU transducers, for example, as described in U.S. Pat. No. 6,492,762 (Pant et al.), granted Dec. 10, 2002, entitled "Ultrasonic transducer, transducer array, and fabrication method." In some embodiments, the transducer layer 172 may include multilayer PVDF films connected electrically in parallel and acoustically in series.

In some embodiments, the transducer layer 172 may have a concave shape to improve the spatial specificity of tFUS neuromodulation. As used herein, the term "concave" refers to being concave toward the target volume 158 in the tissue 154. Lens layer 170 may be used to compensate for the differences between the shape of transducer layer 172 and surface layer 150 of subject 102.

Aperture layer 174 may be used to define the aperture for patch 110. As used herein, the term "aperture" refers to a geometric extent of the active transducer surface in contact with the patient skin through the lens 170. Sampling of active aperture or ultrasound transducer layer 172 may be defined by one or more sampling elements. Each sampling element may be configured to act as a different transducer. Aperture layer 174 may include a plurality of channel conductors 178. Each channel conductor 178 may define a plurality of sampling elements of the aperture in aperture layer 174.

Aperture layer 174 may be coupled to transducer layer 172. Each channel conductor 178 may be operably coupled to a different portion of a surface of transducer layer 172. In some embodiments, an opposite surface of transducer layer 172 may be coupled to lens layer 170.

Aperture layer 174 may be used to provide a fine aperture (e.g., finely sampled) or a coarse aperture (e.g., coarsely sampled). In general, a coarse aperture will use less channels, or ultrasound transducer elements, to provide an ultrasound wavefront than a fine aperture, while still achieving desired target focusing gains (e.g., higher the better) and critical focusing gains (e.g., lower the better). In other words, a fine aperture layer (e.g., aperture layer 174 when configured to provide a fine aperture) may have a greater number of channel conductors than a coarse aperture layer (e.g., aperture layer 174 when configured to provide a coarse aperture).

Each channel conductor 178 may define a conductive surface area having a size or shape different than at least one other channel conductor, particularly when aperture layer 174 is used to provide a coarse aperture. The different sizes or shapes may be determined based on coarse aperture sampling, or channel reduction, described herein. In some embodiments, the conductive surface area of each channel conductor 178 may have a size or shape different than all the other channel conductors.

In some embodiments, aperture layer 174 may be removably coupled to transducer layer 172. For example, one aperture layer 174 may be described as a coarse aperture layer. Upon removing the coarse aperture layer from transducer layer 172, a fine aperture layer may then be coupled to the transducer layer to provide a fine aperture. The fine aperture layer may have a greater number of channel conductors than the coarse aperture layer. Using a fine aperture layer may allow patch 110 to be coupled to a larger number of channels in controller 112. In some embodiments, the fine aperture layer has at least 4 times, at least 8 times, at least 10 times, at least 16 times, or even at least 32 times, the number of channels of the coarse aperture layer. In some embodiments, the coarse aperture layer has at most 64 channels, at most 32 channels, at most 16 channels, at most 8 channels, at most 4 channels, or even at most 1 channel. For example, the fine aperture layer may have 256 channels and the coarse aperture layer may have 8 channels.

In some embodiments, aperture layer 174 may comprise a printed circuit board, particularly a flexible printed circuit board. Conductors on the printed circuit board may be patterned to provide channel conductors 178 on a substrate (e.g., dielectric or electrically insulative material). In some embodiments, the substrate maybe used to form at least part of backing layer 176.

Backing layer 176 may be coupled to aperture layer 174. Backing layer 176 may be formed of any suitable material capable of providing a flexible or semi-rigid patch 110. Backing layer 176 may be formed of electrically insulative material. Backing layer 176 may be configured to control bandwidth and resonance of ultrasound energy transmitted by patch 110. In particular, the material of backing layer 176 and the thickness of backing layer 176 may be selected to help control the bandwidth and resonance of transducer layer 170. In some embodiments, backing layer 176 may be formed of alumina. In some embodiments, backing layer 176 may be formed of one or more thin slab of alumina or flexible circuit boards, which may be used to lower the resonance frequency and control operating bandwidths. In some embodiments, backing layer 176 may have a thickness of about 1 mm or less.

In some embodiments, backing layer 176 may include a plurality of conductive vias 180. The plurality of conductive vias 180 may be coupled to the plurality of channel conductors 178 of aperture layer 174. In particular, each conductive via 180 may operably couple one channel conductor 178 to controller 112 using one or more connectors 124. In some embodiments, conductive vias 180 are not used. For example, in some embodiments, backing layer 176 may be sufficiently thin and may allow the electric field generated from the excitation waveform transmitted through connector 124 to generate a current in channel conductor 178 on the other side of the backing layer. In other words, connector 124 may be operably coupled through electrically-insulating backing layer 176 to aperture layer 174.

As mentioned, each connector 124 may be operably coupled to controller 112. In particular, each connector 124 may be coupled to at least one circulator 130. As illustrated, each connector 124 is coupled to one circulator 130. Each circulator 130 may be operably coupled to at least one transmit circuit 132 and at least one receive circuit 134. As illustrated, each circulator 130 is operably coupled to one transmit circuit 132 and one receive circuit 134.

Circulator 130 may be described as an active circulator. Circulator 130 may use a 3-port network, which passes a first signal from Port 1 (driver) to Port 2 (transducer) but rejects the first signal at Port 3 (ADC) and passes a second signal from Port 2 to Port 3 but rejects the second signal at Port 1. This so-called clockwise circulator action uses a design of the feedback network that creates signal cancellation at even numbered stages (i.e., modulo-2, note the 3 stages are tied in a circular pattern). In some embodiments, circulator 130 may use an OpAmp-based topology (see FIG. 9 using three operational amplifiers), although any suitable circulator topology may be used.

Circulator 130 may include a plurality of ports configured to forward signals received at one port to another port in a "circular" fashion. In the illustrated embodiment, circulator 130 includes a first port, a second port, and a third port. The first port may be configured to receive an excitation waveform from transmit circuit 132. The second port may be configured to provide the excitation waveform (received by the first port) to the transducer layer 170 to provide a transmit ultrasound wavefront. The second may concurrently be configured to receive a reflection waveform from the transducer layer 170 corresponding to a reflection of the transmit ultrasound wavefront during or after providing the excitation waveform. The third port may be configured to provide the reflection waveform to receive circuit 134 during or after receiving the excitation waveform from transmit circuit 132. In some embodiments, receive circuit 134 may be configured to begin receiving the reflection waveform from the third port even while transmit circuit 132 is providing the transmit excitation waveform to the first port.

Using one or more circulators 130, controller 112 may be configured to provide a continuous excitation waveform to transducer layer 170 on each channel even while receiving a continuous reflection waveform on the same channels (e.g., using the same portions of the transducer layer and the same channel conductors 178). As used herein, the term "continuous excitation waveform" refers to a waveform that, in contrast to a series of pulses or bursts, does not use breaks in transmission to detect a reflection waveform.

Each transmit circuit 132 may be configured to provide an excitation waveform vector to the plurality of channel conductors 178 (e.g., an excitation waveform for each of one or more channel conductors) to generate the transmit ultrasound wavefront with transducer layer 170.

Each receive circuit 134 may be configured to receive a reflection waveform vector from the plurality of channel conductors 178 (e.g., a reflection waveform from each of one or more channel conductors) that correspond to the reflected ultrasound wavefront received by the transducer layer 170.

Controller 112 may be described as having one or more channel interfaces 182. Each channel interface 182 may include one or more transmit circuits 132, one or more receive circuits 134, and one or more circulators 130. As illustrated, each channel interface 182 includes one transmit circuit 132, one receive circuit 134, and one circulator 130.

Each channel may be described as including one or more interfaces 182, one or more connectors 124, optionally one or more conductive vias 180, one or more channel conductors 178, and at least a portion of transducer layer 170. As illustrated, each channel includes one channel interface 182, one connector 124, one optional conductive via 180, one channel conductor 178, and a portion of transducer layer 172.

Although only three channels and channel interfaces 182 are shown, any number of channel interfaces 182 may be used to provide imaging or therapy using patch 110 depending on the particular application.

Patch 110 may define a transducer bandwidth. Obstacle 152 may define an obstacle bandwidth. The transducer bandwidth and/or the obstacle bandwidth may be used to define an overall usable bandwidth. Use of the entire usable bandwidth may be referred to herein as "wideband," whereas use of a fraction of the bandwidth may be referred to as "narrowband." A wideband or broadband waveform may use several narrow bands, whereas a narrowband waveform may use only one band.

Figure 4:
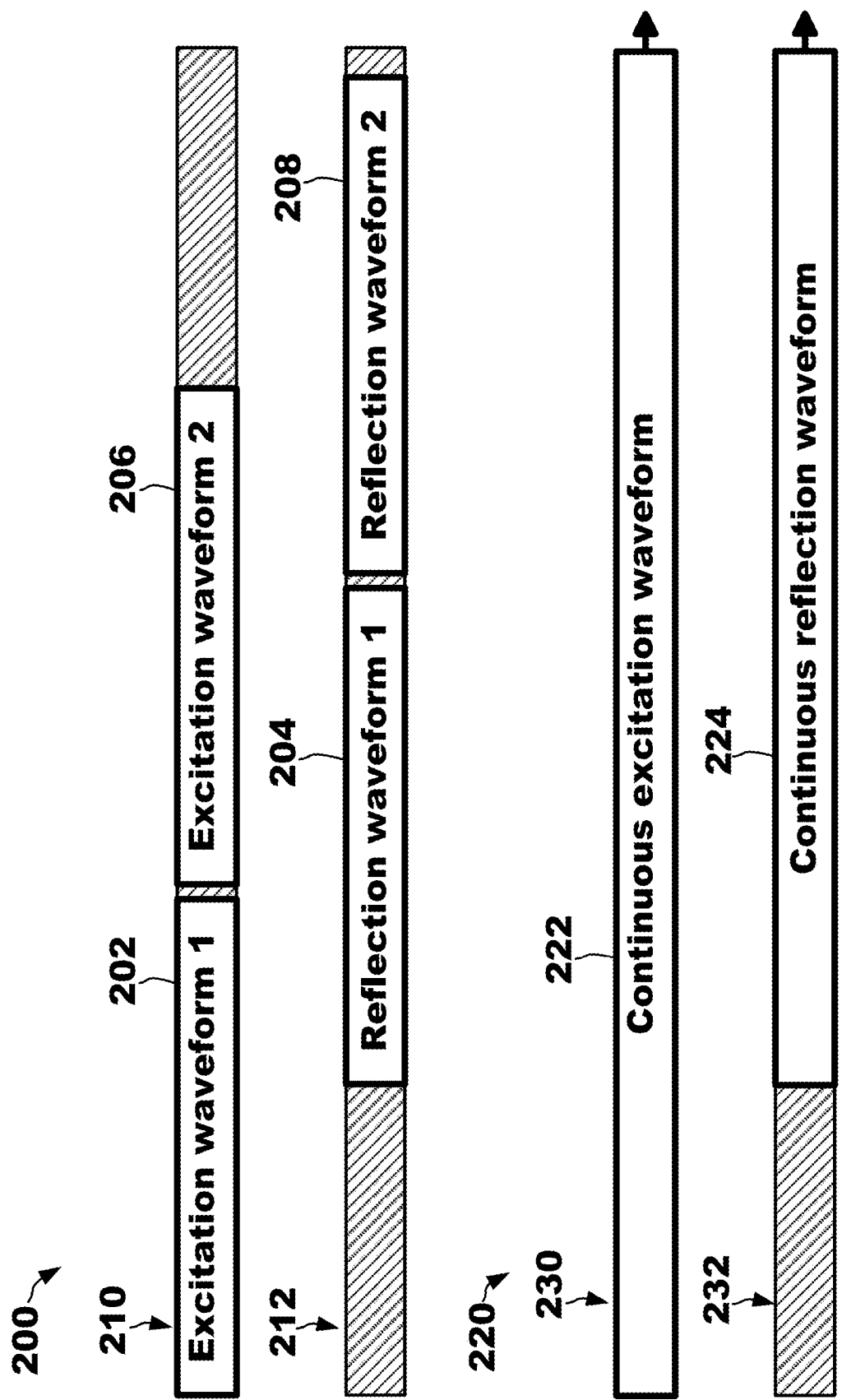
FIG. 4 is a diagram showing discrete excitation waveforms and continuous excitation waveforms that may be provided on a channel of the systems of FIGS. 1-3 to a transducer element and expected reflection waveforms received on the same channel.

FIG. 4 is a diagram showing illustrative discrete excitation waveforms (e.g., pulses) and continuous excitation waveforms that may be provided on a channel of an ultrasound transducer system of the present application (e.g., using controller 112 having circulator 130) to a transducer element and expected reflection waveforms received on the same channel.

As illustrated, over a time period, channel 200 may be used to transmit excitation waveforms 202, 206 and receive reflection waveforms 204, 208. For convenience, channel 200 is depicted to show a transmit portion 210 of channel 200 (e.g., corresponding to transmit circuit 132 ) and a receive portion 212 of channel 200 (e.g., corresponding to receive circuit 134 ) in the respective channel 210, 212. Channel 200 may be used to transmit waveforms 202, 206 in sequence. Each waveform 202, 206 may be described as an ultrasound pulse or a discrete waveform. For example, a break exists between waveforms 202, 206, even if the break is small compared to (e.g., shorter in duration than) the overall duration of one or both waveforms.

Using a system of the present application (e.g., using controller 112 having circulator 130), channel 200 may begin receiving reflection waveform 204 before excitation waveform 202 is finished transmitting on the channel. Channel 200 may also begin receiving reflection waveform 208 before excitation waveform 206 is finished transmitting on the channel.

In comparison to channel 200, channel 220 is illustrated being used to transmit excitation waveform 222 and receive reflection waveform 224. Channel 220 is depicted to show a transmit portion 230 and a receive portion 232 of channel 200. Each waveform 222, 224 may be described as a continuous waveform in the respective channel 230, 232. Using a system of the present application, channel 220 may begin receiving continuous reflection waveform 224 while continuous excitation waveform 222 is still being transmitted on the channel.

Figure 5:
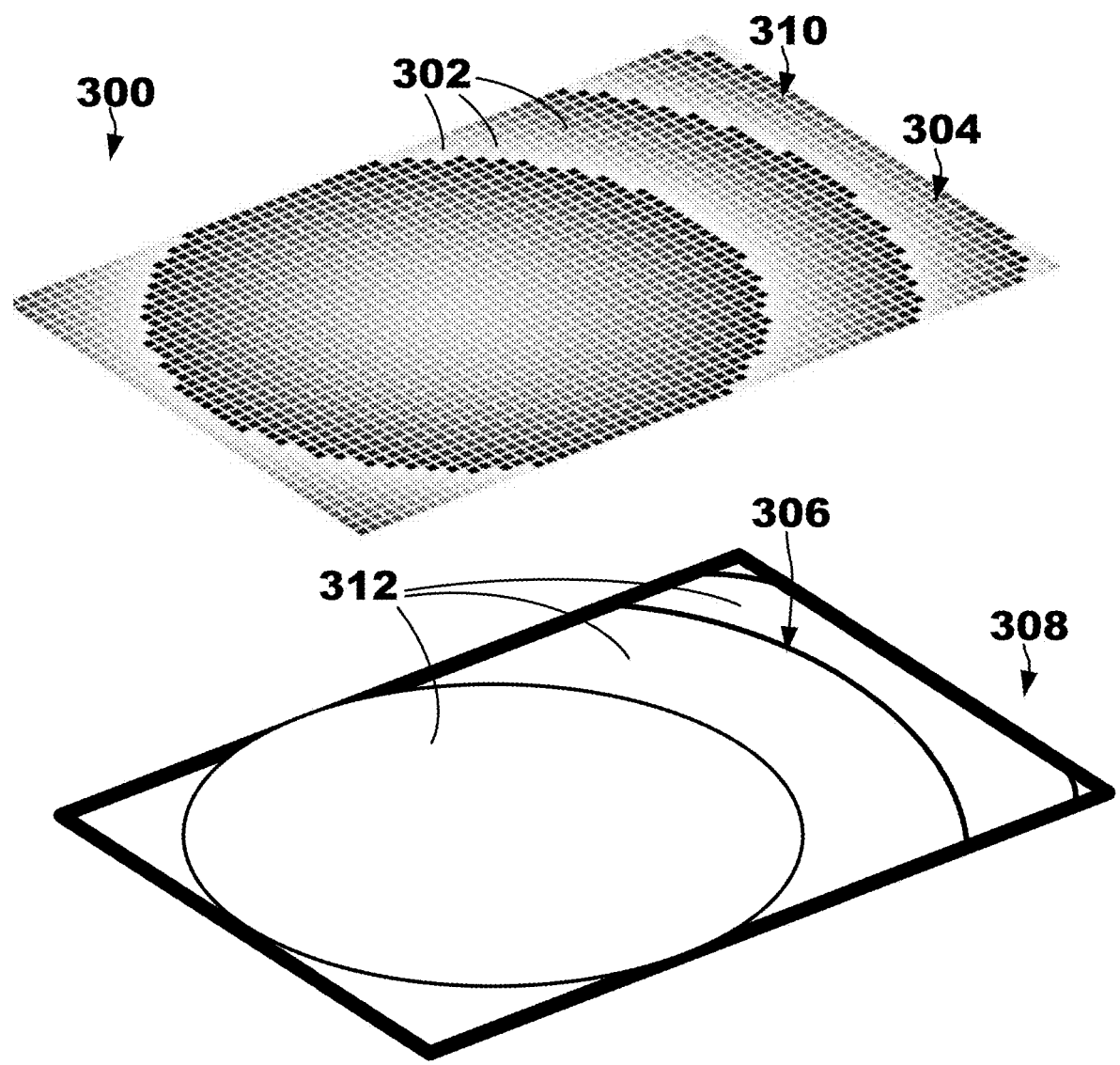
FIG. 5 is a schematic illustration of a transducer layer being used with a fine aperture to produce an optimal excitation vector for use with, e.g., the systems of FIGS. 1-3.

FIG. 5 is a schematic illustration of an illustrative transducer layer 300 being used with fine aperture 304 to produce excitation vector 310. Excitation vector 310 may be used to produce reduced-element excitation vector 306 and a reduced number of sampling super elements 312, which may be used to define coarse aperture 308. As illustrated, the fine aperture uses a plurality of fine sampling elements 302 shown as small squares or rectangles, although any suitable shape may be used. In some embodiments, fine sampling elements 302 may be divided evenly throughout transducer layer 300. The number of fine sampling elements 302 for fine aperture 304 may number in the hundreds or even thousands. Fine sampling elements 302 may be selected using a uniform sampling lattice within array aperture 304, which may be used to maintain uniformity.

Fine aperture 304 may be used, for example, in a narrow frequency band, to determine optimal excitation vector 310 using narrowband synthesis. Narrowband synthesis may also use identified target points and critical points to determine optimal excitation vector 310.

Each element of excitation vector 310 may be described as a narrowband waveform. When generating an optimal excitation vector 310 for a narrowband in the bandwidth of the transducer and/or obstacle, each waveform may be in the same narrow frequency band and may have the same or similar frequency content. The differences in the narrowband waveforms of excitation vector 310 are shown as different shading of sampling elements 302 of fine aperture 304. In the illustrated embodiment, the shading represents the different phases of the narrowband waveform.

Sampling elements 302 may be clustered based on the narrowband waveforms of excitation vector 310. In particular, the sampling elements 302 of excitation vector 310 may be clustered based on phase. Similar phases may be grouped together. In particular, the clustering of sampling elements 302 may be performed based on the phase distribution resulting from narrowband synthesis at or around a selected frequency. In some embodiments, the narrowband selected may include a midrange within the bandwidth of the transducer and/or the bandwidth of the obstacle. In addition, or alternatively, the frequency band selected may include a high range within the bandwidth of the transducer and/or obstacle. Selecting a frequency band in the high range of the bandwidth may represent a worst-case design scenario. Phase variations are typically higher at higher frequencies or shorter wavelengths. In some embodiments, using the high range may be described as a conservative design, which may result in more channels (e.g., using more super elements 312 in coarse aperture 308 ) after clustering compared to using the midrange, which may result in a further reduction in channels. In some cases, the difference may be insignificant to performance. In some embodiments, similar phases are defined as phases within a range of plus or minus 45 degrees at the selected frequency.

When clustered, the sampling elements 302 may be combined or grouped into super elements 312. As illustrated, reduced-element excitation vector 306 includes only a few super elements 312 compared to the hundreds of sampling elements 302 of fine aperture 304. The super elements 312 may define a coarse aperture 308.

Figure 6:
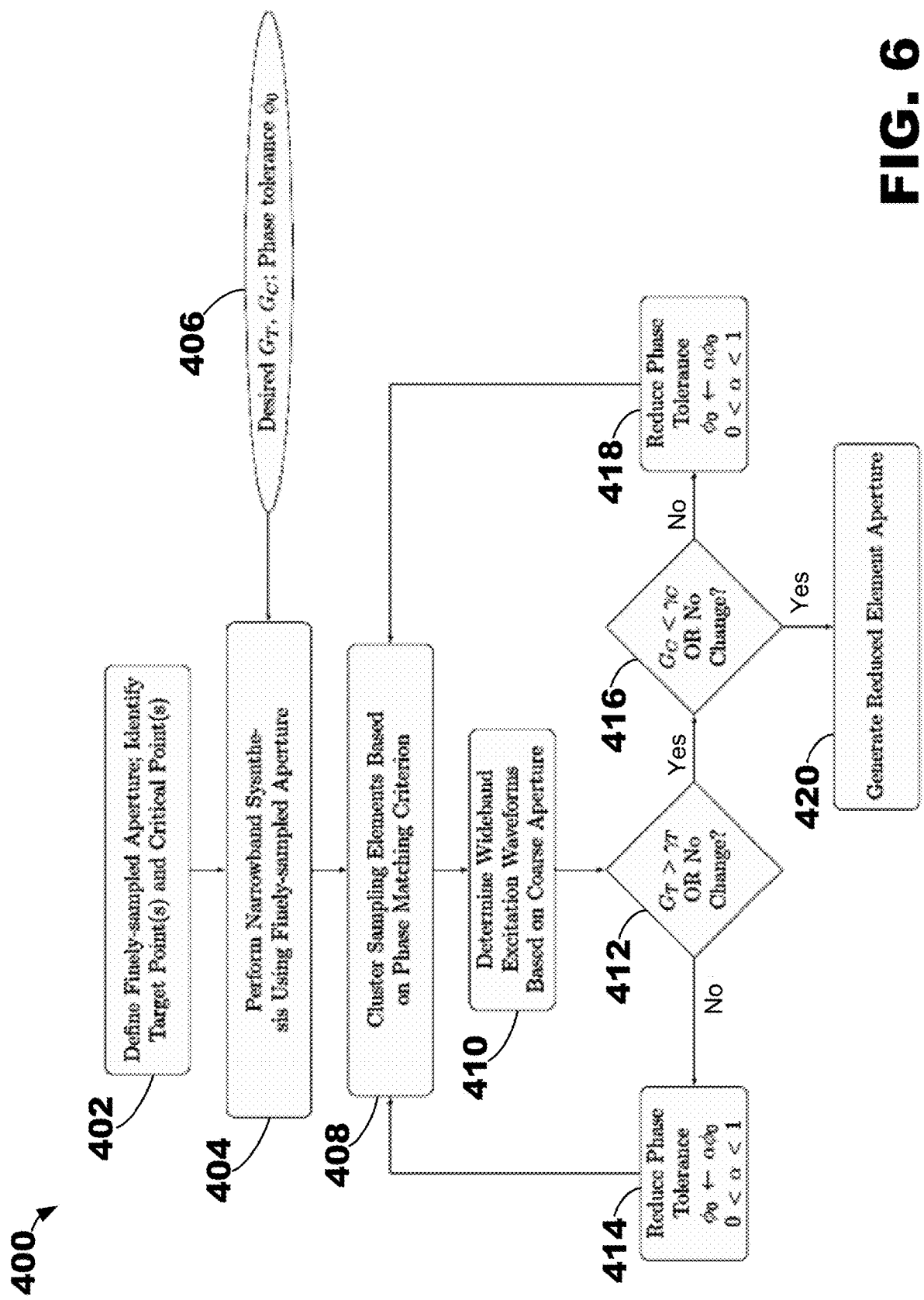
FIG. 6 is a flowchart showing a method of generating aperture sampling with reduced channel count for use with, e.g., the systems of FIGS. 1-3.

FIG. 6 is a flowchart showing an illustrative method 400 of generating aperture sampling with reduced channel count (e.g., coarse aperture). Method 400 may include defining a finely-sampled aperture (e.g., fine aperture), identifying target points, and/or identifying critical points 402. The finely-sampled aperture may have a plurality of sampling elements. Each sampling element may correspond to a different region of an ultrasound transducer surface (e.g., a different portion of an ultrasound transducer layer). Target points and critical points may be identified using imaging information (e.g., ultrasound imaging).

Method 400 may include determining a desired target focusing gain, a desired critical focusing gain, and/or a threshold phase tolerance 406.

Using information from processes 402, 406 as inputs, method 400 may include performing narrowband synthesis 404 to produce an optimal excitation vector that avoids depositing ultrasound energy in critical points (e.g., minimizes critical focusing gain) and favors depositing ultrasound energy in target points (e.g., maximizes target focusing gain). The optimal excitation vector may include an element, or narrowband waveform, for each of the sampling elements of the finely-sampled aperture. Narrowband synthesis may be performed in a mid-range of high-range of the transducer and/or obstacle bandwidth. One example algorithm for narrowband synthesis is shown as algorithm 450 in FIG. 7. In particular, at least one propagation operator may be determined based on the finely-sampled aperture and at least one target point. One propagation operator may be determined for each target point and/or each critical point. The optimal excitation vector may be determined based on each of the propagation operators.

In general, method 400 may cluster sampling elements of the finely-sampled aperture into groups of two or more sampling elements based on similar narrowband excitation waveforms in the excitation waveform vector. Clustering may be performed on one or more narrowband excitation waveform vectors covering the transducer and/or obstacle bandwidth. Clustering may be described as an optimization problem.

In some embodiments, in human transcranial application, the transducers and the skull may combine to limit the overall bandwidth to about 1.5-2 MHz (0.5-2.5 MHz). Aperture sampling may be performed by combining results from, for example, 100 kHz bands covering the frequency range of 500 kHz to 2.5 MHz. Within each band, clustering (e.g., irregular size or shape sampling) may be performed based on phase alignment between sampling-element waveforms. The amplitude of each waveform can be small as long as the energy is sufficiently high, which may depend on having a sufficiently long pulse duration (e.g., long pulse duration of continuous waveform). In some embodiments, a long pulse duration waveform may be at least 1 millisecond.

In some embodiments, method 400 may include clustering the sampling elements of the finely-sampled aperture 408 using information from the optimal excitation vector. In particular, sampling elements may be clustered based on phase matching criterion, such as the phase tolerance. Each element of optimal excitation vector may correspond to a waveform. The phase of each waveform may be compared to other waveforms in neighboring sampling elements. The reduced-element optimal excitation vector may be used to generate a coarse aperture having fewer sampling elements based on groups of the fine sampling elements of the finely-sampled aperture (e.g., based on phase).

Method 400 may include determining wideband excitation waveforms using the coarse aperture 410. In particular, optimal excitation vectors may be generated for all narrowband frequencies in the transducer and/or obstacle bandwidth. The narrowband waveforms of the optimal excitation vectors may be combined into a plurality of excitation waveforms. One excitation waveform may be generated for each sampling element of the coarse aperture (e.g., each super element of the coarse aperture).

The wideband excitation waveforms used for imaging and/or therapy may be optimized using elongated (e.g., long pulse duration or continuous waveform) wideband arbitrary waveforms for exciting the transducer elements. Each of the wideband excitation waveforms may have desirable correlation properties for the particular target volume.

Using wideband excitation waveforms may mitigate some undesirable effects of coarse sampling of the aperture. For example, a coarsely sampled aperture excited using narrowband waveforms may produce undesirably high grating lobes, which may degrade both the therapeutic and imaging performance.

The focusing gains may be determined for each of the target points (e.g., target focusing gains $G_T$) and critical points (e.g., critical focusing gains $G_C$) using the wideband excitation waveforms and the coarse aperture. These focusing gains may be described as wideband, or broadband, focusing gains.

Method 400 may include determining a target focusing gain $G_T$ (e.g., for each target point) and comparing the target focusing gain to a desired target focusing gain $\gamma_T$ (e.g., a target focusing gain threshold), a previously determined target focusing gain $G_T$, and/or a critical focusing gain obtained using the finely-sampled aperture 412.

If $G_T > \gamma_T$, if there is no change in $G_T$, and/or the difference between the target focusing gains for coarse and fine apertures is acceptable, then method 400 may branch to determining a critical focusing gain $G_C$ (e.g., for each critical point) and comparing the critical focusing gain to a desired critical focusing gain $\gamma_C$ (e.g., a critical focusing gain threshold), a previously determined critical focusing gain $G_C$, and/a critical focusing gain obtained using the finely-sampled aperture 416. Otherwise (e.g., if the comparison or difference is unacceptable), method 400 may branch to reducing the phase tolerance 414 and reclustering sampling elements based on the new, or reduced, phase tolerance 408, which may increase the number of sampling elements (e.g., super elements) in a new coarse aperture.

When branching to process 416, if $G_C < \gamma_C$, if there is no change in $G_C$, and/or if the difference between the critical focusing gains for coarse and fine apertures is acceptable, then method 400 may branch to generating a reduced element aperture based on the current phase tolerance. Otherwise (e.g., if the comparison or difference is unacceptable), method 400 may branch to reducing phase tolerance 418 and reclustering sampling elements based on the new, or reduced, phase tolerance 408, which may increase the number of sampling elements (e.g., super elements) in a new coarse aperture.

In general, if the focusing gain based on the reduced-element excitation vector used to generate the coarse aperture does not meet the specified value, the clustering process is repeated with more stringent phase criterion.

FIG. 7 is pseudocode of an illustrative iterative algorithm 450 that may be used to provide optimal sampling elements for an aperture. Optimal array design methods for the maximization of the therapeutic (focusing) gain in the target volume or therapeutic operating field (ThxOF) (e.g., target volume 158) for concave arrays may be used, for example, as described in E. Ebbini, *Deep Localized Hyperthermia with Ultrasound Phased Arrays Using the Psudoinverse Pattern Synthesis Method*, PhD thesis, University of Illinois, 1990, E S Ebbini and C A Cain, *Experimental evaluation of a prototype cylindrical section ultrasound hyperthermia phased-array applicator*, IEEE TRANSACTIONS ON ULTRASONICS FERROELECTRICS AND FREQUENCY CONTROL, 38(5):510-520, September 1991, or E. S. Ebbini, H. Yao, and A. Shrestha, *Dual-mode ultrasound arrays for image-guided surgery*, Ultrasonic Imaging, 28:65-82, April 2006.

The aperture size, radius of curvature, element size, and spacing may be chosen based on maximizing the focusing gain throughout the ThxOF, which may be defined by the depth and extent of the target volume, e.g., a cancer tumor. The imaging field of view (IxFoV) (e.g., ultrasound FOV 156) may be maximized using an optimized DMUA design, for example, as described in E. S. Ebbini, H. Yao, and A. Shrestha, *Dual-mode ultrasound arrays for image-guided surgery*, Ultrasonic Imaging, 28:65-82, April 2006, or Y Wan and E S Ebbini, *Imaging with concave large-aperture therapeutic ultrasound arrays using conventional synthetic-aperture beamforming*, IEEE Trans. UFFC, 55(2):368-383, February 2008. A pseudoinverse pattern synthesis method, for example, as described in E S Ebbini and C A Cain, *Multiple-focus ultrasound phased array pattern synthesis—Optimal driving signal distributions for hyperthermia*, IEEE TRANSACTIONS ON ULTRASONICS FERROELECTRICS AND FREQUENCY CONTROL, 36(5):540-548, September 1989, may be used, to solve for the array excitation pattern assuming a known propagation operator $H_T$ between N array elements and M control (target) points for a specified vector of complex pressures, $p_T$ of size M×1. The optimization problem may be used to adjust, compensate, or account for the presence of obstacles (e.g., obstacle 152, such as the skull) or critical points (e.g., the rib cage when targeting liver tumors) in the path of the beam. These critical points may be used to define another propagation operator, $H_C$, from the array elements to the set of target points which may be dense. As used herein, target points may also be described as control points.

With these parameters, an iterative aperture-sampling algorithm for defining the DMUA elements according to algorithm 450 may be used. The algorithm may be initialized by specifying the one or more target points and a Nyquist-sampled aperture (e.g., finely-sampled aperture) on a planar or nonplanar surface (e.g., surface of transducer layer 172 ), for example, as described in E. Ebbini, *Deep Localized Hyperthermia with Ultrasound Phased Arrays Using the Psudoinverse Pattern Synthesis Method*, PhD thesis, University of Illinois, 1990, which defines $H_T^{(0)}$ and) $H_C^{(0)}$. The procedure in algorithm 450 may be called, which produces or provides an optimal excitation vector $\mu_{opt}^{(0)}$.

In addition to providing the optimal excitation vector, algorithm 450 may use clustering and focusing gain evaluation to reduce channel count. In particular, the size of the optimal excitation vector may be reduced by clustering neighboring elements with "sufficiently close" phase and amplitude driving signals (e.g., process 408 of FIG. 6), which will produce new propagation operators, $H_T^{(1)}$ and $H_C^{(1)}$.

The quality of the field patterns generated by the coarse sampling may be checked against the fully-sampled aperture (e.g., Nyquist-sampled or finely-sampled aperture). For example, one or more target and/or critical focusing gains may be determined using Equation 1, where $(\cdot)^H$ is the Hermitian transpose. Based on comparing the focusing gains for the coarsely sampled and the fully sampled apertures, the clustering process may be refined (if the loss in $G_T^{(i)}$ is unacceptable) or continued (if $G_T^{(i)}$ is within acceptable limits). The iterative process may continue until a desired reduction in channel count is achieved, or no further reduction in channel count can be achieved, for a given $G_T$ specification.

$$G_T^{(i)} = \frac{p_T^H p_T}{u_{opt}^{(i)H} u_{opt}^{(i)}} = \frac{p_T^H p_T}{p_T^H (H_T W_C^{-1} H_T^H)^\dagger p_T} \quad (1)$$

Figure 8:
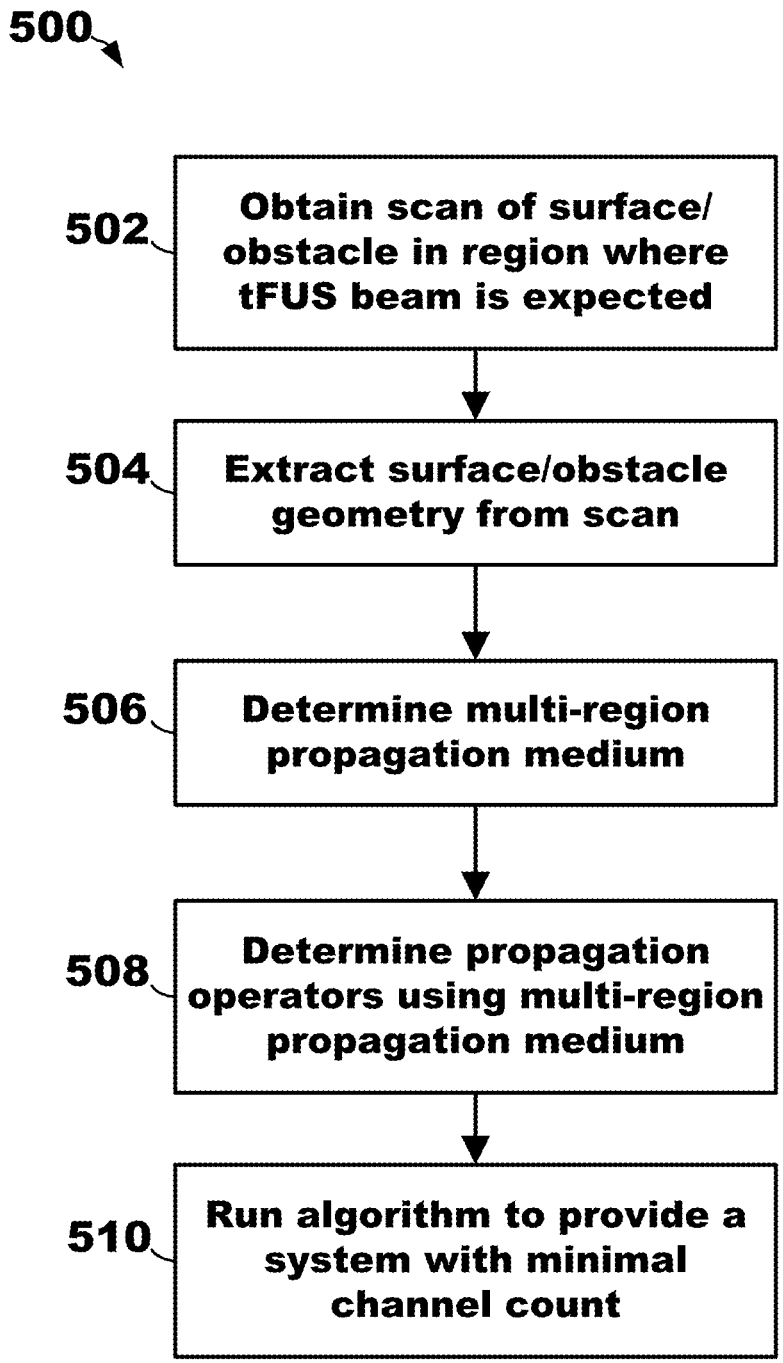
FIG. 8 is a flowchart showing a method for designing a patch transducer array having a reduced channel count for use with, e.g., the systems of FIGS. 1-3.

FIG. 8 is a flowchart showing an illustrative method 500 for designing a patch transducer array (e.g., patch 110 of FIGS. 1-3) having a reduced channel count (e.g., low channel count).

Method 500 may include obtaining a scan of a surface and/or obstacle 502. In particular a 3D scan of the skull (e.g., obstacle 152 of FIG. 3) may be obtained in the region where the tFUS beam (e.g., ultrasound FOV 156 of FIG. 3) is expected to access the brain (e.g., of subject 102 of FIG. 3). An illustrative 3D scan is shown in the rendering 900 of FIG. 12. A high channel-count controller 112 (FIGS. 1-3) may be used with patch 110 for this purpose.

Method 500 may include extracting surface geometry 504. In particular, skull surface geometry may be extracted using appropriate 3 D rendering (e.g., using MATLAB or Slicer).

Method 500 may include determining a multi-region propagation medium 506. In particular, a 3-region propagation medium may be determined for the estimation of $H_T^{(0)}$ and $H_C^{(0)}$ using Regions 1, 2, and 3 as described herein.

Region 1: The scalp (e.g., surface layer 150 of FIG. 3) with lateral and elevation extent (e.g., area having width and elevation) sufficiently larger than the size of the DMUA aperture used to achieve an acceptable focusing gain $G_T^{\square}$ (e.g., area of patch 110 shown in FIG. 1).

Region 2: The skull (e.g., obstacle 152 of FIG. 3) with similar lateral and elevation extent as in Region 1.

Region 3: The brain tissue volume (e.g., tissue 154 of FIG. 3) with similar lateral and elevation extent as in Regions 1 and 2. The axial extent (e.g., depth) will include the target voxel(s) and sufficient volume distal to the target voxel(s) to account for the divergence of tFUS.

Method 500 may include computing propagation operators using the multi-region propagation medium 508. In particular, an appropriate numerical method may be used to compute the propagation operators. For example, a boundary element method as described in Y. Y. Botros, J. L. Volakis, P. VanBaren, and E. S. Ebbini, *A hybrid computational model for ultrasound phased-array heating in presence of strongly scattering obstacles*, IEEE Trans Biomed Eng, 44(11):1039-1050, November 1997, may be used, although other approaches, including the angular spectrum method as described in Joseph W. Goodman, *Introduction to Fourier Optics*, Roberts & Company, 2005, and its extension to inhomogeneous media as described in U Vyas and D A Christensen, *Extension of the angular spectrum method to calculate pressure from a spherically curved acoustic source*, 130:2687-93, J Acoust Soc Am., 2011, may also be used, which may be described as being simpler in some cases.

Method 500 may include running an algorithm to provide a system with minimal channel count 510. In particular, algorithm 450 may be run iteratively with clustering and focusing gain evaluation to provide design of system 100 and patch 110 of FIGS. 1-3 with low channel count (e.g., DMUA tFUS applicator with minimum or substantially minimal channel count).

While the present disclosure is not so limited, an appreciation of various aspects of the disclosure will be gained through a discussion of the specific examples and illustrative embodiments provided below.

EXAMPLES

Example 1

Full-Duplex DMUA System for tFUS Using Diplexer

Figure 10:
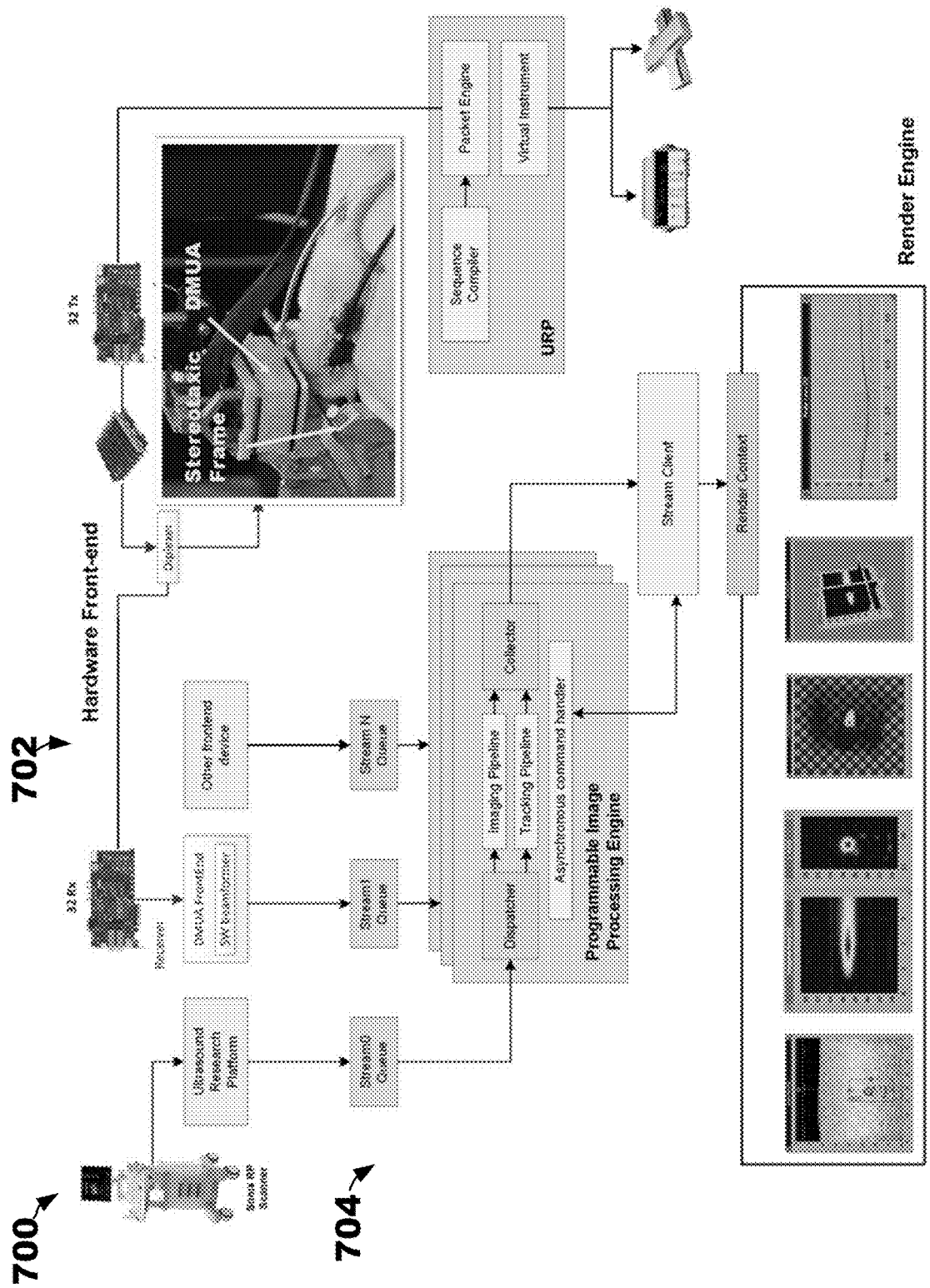
FIG. 10 is a schematic illustration showing a DMUA system with a diplexer and a supporting multi-stream software architecture being used for an in vivo experiment with a rat connected to an anesthesia system and the head fixed with respect to a stereotaxic frame. In the illustration, the DMUA system includes a render engine that may be used for real-time visualization of DMUA images with overlay of results from a tracking pipeline.

The DMUA system as described in A. J. Casper, D. Liu, J. R. Ballard, and E. S. Ebbini, *Real-time Implementation of a Dual-Mode Ultrasound Array System: In Vivo Results*, Biomedical Engineering, IEEE Transactions on, Pre-publication, May 2013(99):1-1, 2013, and the in vivo results in rat brain as described in Alyona Haritonova, Dalong Liu, and Emad S Ebbini, *In Vivo application and localization of transcranial focused ultrasound using dual-mode ultrasound arrays*, 62:2031-2042, 2015, were modified using a 3-axis motorized DMUA holder together with synchronized synthetic aperture imaging, as shown in FIG. 10, to obtain 3D ultrasound images of the skull and target brain region before each treatment. The modified DMUA system was used to identify suture lines (bregma, lambda and medial), which were used to position the DMUA in a proper targeting position as described in D. Liu, K. Schaible, W. Low, and E. S. Ebbini, *Three-dimensional image guidance for transcranial focused ultrasound therapy*, 2017 IEEE 14th International Symposium on Biomedical Imaging (ISBI 2017), pages 916-919, April 2017. In FIG. 10, the ultrasound system 700 including the DMUA system 702 and supporting multi-stream software architecture 704 are illustrated. The DMUA system 702 prototype is shown during an in vivo experiment with the rat connected to the anesthesia system and the head fixed with respect to a stereotaxic frame. The render engine was used for real-time visualization of DMUA images with overlay of results from the tracking pipeline.

Figure 11:
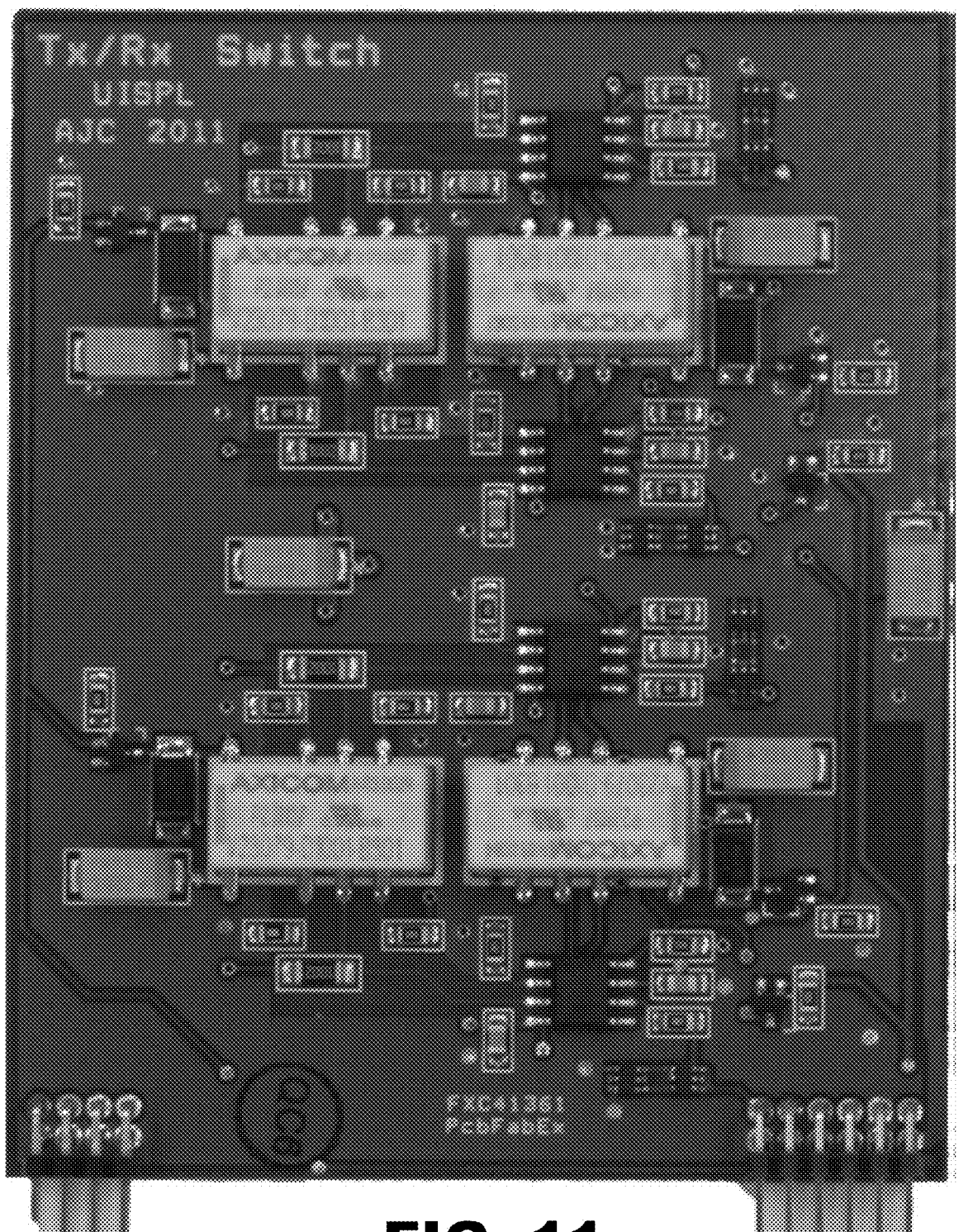
FIG. 11 is an image of a 4 -channel active diplexer circuit board used in the DMUA system of FIG. 10.

The DMUA system 702 used an active RF transmit-receive switch to allow for pulse-echo imaging with high levels of isolation suitable for high dynamic range imaging. FIG. 11 shows an image of a 4-channel active diplexer circuit board 800 that was used with the DMUA system 702. The circuit board 800 was designed to provide: 1) a programmable high-voltage isolation/attenuation (transducer side), 2) buffering with programmable gain (transducer to ADC), and 3) over-voltage protection of the ADC. The circuit was thoroughly tested in a variety of applications, including high power ablative experiments. This was accomplished uniformly in the 0.3-10 MHz band using 7 precision resistors, 2 high-speed relays, 4 diodes, and 1 OpAmp per channel.

Example 2

Full-Duplex DMUA System for tFUS and Transcranial Neuromodulation Using Full-Duplex Transmit-Receive Circuitry (e.g., Circulators)

Figure 9:
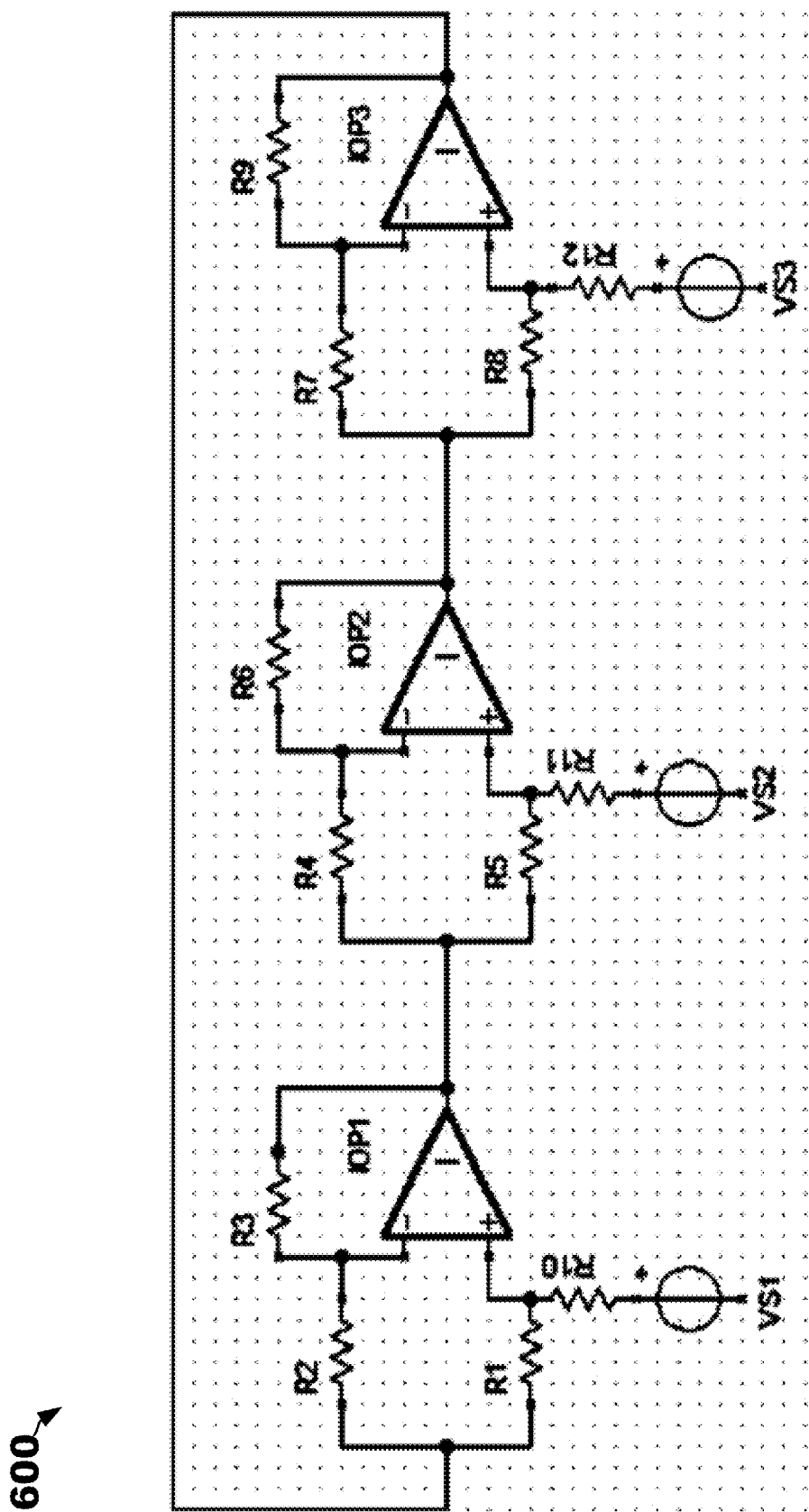
FIG. 9 is a schematic illustration showing an OpAmp-based topology for an active circulator for use with, e.g., the system of FIGS. 1-3.

Topology 600 shown in FIG. 9 will be used to realize an active circulator. The active diplexer circuit on circuit board 800 shown in FIG. 11 and used in Example 1 will be replaced with active circulator circuit 600 of FIG. 9 to provide a circulator DMUA system. The active diplexer circuit 600 will have all the components needed for using the circulator. The components are expected to satisfy the bandwidth as well as the power targets.

The active circulator will be a 3-port network, which will pass the signal from Port 1 (driver) to Port 2 (transducer) but reject the signal at Port 3 (ADC). Similarly, the active circulator will pass the signal from Port 2 to Port 3 but reject the signal at Port 1. This so-called clockwise circulator action will use a design of the feedback network that creates signal cancellation at even numbered stages (i.e., modulo-2, note the 3 stages are tied in a circular pattern).

The level of isolation using the active circulator will be tested.

Acoustic Characterization of Full-Duplex Operation In Vivo

The full-duplex operation of the DMUA will be acoustically characterized. In vivo experiments will be performed for collecting data using the diplexer-based DMUA system of Example 1 and using the circulator DMUA system with the proposed circulator-based transmit-receive circuitry as described herein. The circulator circuitry will be designed and fabricated on printed-circuit boards pin-compatible to the diplexer board 800 shown in FIG. 11.

Example 3

DMUA Systems for Continuous Delivery, Monitoring, and Control of Localized tFUS In Vivo Using Light-Weight, Conformable Arrays Light-weight, site-specific arrays optimized for targeting specific circuit(s) within the brain will be designed and fabricated. These wearable patch-like arrays will utilize low-power drivers and processors for generating tFUS neuromodulation patterns with high spatial localization. These arrays and DMUA system of Example 2 will be used to test continuous delivery, monitoring, and control of localized tFUS in vivo through the temporal bone into an area that may traditionally be targeted by a deep-brain stimulation (DBS) electrode.

While the design and fabrication for the in vivo rat model is described herein, parallel studies using human skull samples and a realistic human head phantom (TruePhantom, Toronto, Ontario) will be performed. For the rat model, patch DMUA transducers will be produced to dimensions of $10 \times 6 \times 2$ mm$^3$ in the lateral, elevation, and axial directions, respectively. These apertures are expected to be effectively sampled using 8-10 channels for most targets in the rat brain.

Patch DMUA Design Optimization and Validation

The DMUA design algorithm described herein will be used to achieve substantial reduction in the number of channels. For patch DMUA design optimization and validation, optimal array design methods for the maximization of the therapeutic (focusing) gain in the target volume or therapeutic operating field (ThxOF), which have been applied to a number of concave array transducers, as described in E. Ebbini, *Deep Localized Hyperthermia with Ultrasound Phased Arrays Using the Psudoinverse Pattern Synthesis Method*, PhD thesis, University of Illinois, 1990, E S Ebbini and C A Cain, *Experimental evaluation of a prototype cylindrical section ultrasound hyperthermia phased-array applicator*, IEEE TRANSACTIONS ON ULTRASONICS FERROELECTRICS AND FREQUENCY CONTROL, 38(5):510-520, September 1991, or E. S. Ebbini, H. Yao, and A. Shrestha, *Dual-mode ultrasound arrays for image-guided surgery*, Ultrasonic Imaging, 28:65-82, April 2006, will be used. Briefly, the aperture size, radius of curvature, element size, and spacing will be chosen based on maximizing the focusing gain throughout the ThxOF, which will be defined by the depth and extent of the target volume, e.g., a cancer tumor. The imaging field of view (IxFoV) will be maximized using an optimized DMUA design as described in E. S. Ebbini, H. Yao, and A. Shrestha, *Dual-mode ultrasound arrays for image-guided surgery*, Ultrasonic Imaging, 28:65-82, April 2006, and Y Wan and E S Ebbini, *Imaging with concave large-aperture therapeutic ultrasound arrays using conventional synthetic-aperture beamforming*, IEEE Trans. UFFC, 55(2):368-383, February 2008. A pseudoinverse pattern synthesis method as described in E S Ebbini and C A Cain, *Multiple-focus ultrasound phased array pattern synthesis—Optimal driving signal distributions for hyperthermia*, IEEE TRANSACTIONS ON ULTRASONICS FERROELECTRICS AND FREQUENCY CONTROL, 36(5):540-548, September 1989, will be used to solve for the array excitation pattern assuming a known propagation operator $H_T$ between N array elements and M control (target) points for a specified vector of complex pressures, $p_T$ of size M×1. The optimization problem will account for the presence of obstacles or critical points (e.g., the rib cage when targeting liver tumors) in the path of the beam. These critical points will define another propagation operator, $H_C$, from the array elements to the (possibly dense) set of target, or control, points.

With these parameters, an iterative aperture-sampling algorithm for defining the DMUA elements is given in algorithm 450 (FIG. 7). The algorithm will be initialized by specifying the target point(s) and a Nyquist-sampled aperture on a planar or nonplanar surface, as described in E. Ebbini, *Deep Localized Hyperthermia with Ultrasound Phased Arrays Using the Psudoinverse Pattern Synthesis Method*, PhD thesis, University of Illinois, 1990, which defines $H_T^{(0)}$ and $H_C^{(0)}$. The procedure in algorithm 450 will be called, which will produce an optimal excitation vector, $u_{opt}^{(0)}$. The size of this vector may be reduced by clustering neighboring elements with "sufficiently close" phase and amplitude driving signals (e.g., within plus or minus 45 degrees), which will produce new propagation operators, $H_T^{(1)}$ and $H_C^{(1)}$. The quality of the field patterns generated by the coarse sampling will be checked against the fully-sampled aperture (e.g., Nyquist-sampled aperture). In particular, the focusing gains will be determined using Equation 1, where $(\cdot)^H$ is the Hermitian transpose. Based on comparing the focusing gains for the coarsely sampled and the fully sampled apertures, the clustering process can be refined (if the loss in $G_T^{(i)}$ is unacceptable) or continued (if $G_T^{(i)}$ is within acceptable limits). The iterative process will continue until no further reduction in channel count can be achieved for a given $G_T$ specification.

The design algorithm will be modified to account for the skull geometry as follows:

Step 1: Obtain 3D scan of the skull in the region where the tFUS beam is expected to access the brain similar to the scan render 900 shown in FIG. 12. A laboratory prototype DMUA can be used for this purpose.

Step 2: Extract skull surface geometry using appropriate 3D rendering (e.g., using MATLAB or Slicer).

Step 3: Build a 3-region propagation medium for the estimation of $H_T^{(0)}$ and $H_C^{(0)}$ using Regions 1, 2, and 3 as described herein.

Region 1: The scalp with lateral and elevation extent (e.g., area having width and elevation) sufficiently larger than the size of the DMUA aperture used to achieve an acceptable focusing gain $G_T^\square$.

Region 2: The skull with similar lateral and elevation extent as in Region 1.

Region 3: The brain tissue volume with similar lateral and elevation extent as in Regions 1 and 2. The axial extent (e.g., depth) will include the target voxel(s) and sufficient volume distal to the target voxel(s) to account for the divergence of tFUS.

Step 4: Use appropriate numerical method to compute the propagation operators. For example, a boundary element method as described in Y. Y. Botros, J. L. Volakis, P. VanBaren, and E. S. Ebbini, *A hybrid computational model for ultrasound phased-array heating in presence of strongly scattering obstacles*, IEEE Trans Biomed Eng, 44(11):1039-1050, November 1997, may be used, but simpler approaches, including the angular spectrum method as described in Joseph W. Goodman, *Introduction to Fourier Optics*, Roberts & Company, 2005, and its extension to inhomogeneous media as described in U Vyas and D A Christensen, *Extension of the angular spectrum method to calculate pressure from a spherically curved acoustic source*, 130:2687-93, J Acoust Soc Am., 2011, may also be used.

Step 5: Run algorithm 450 (FIG. 7) iteratively with clustering and focusing gain evaluation to realize a DMUA tFUS applicator with minimum or substantially minimal channel count.

Figure 13A:
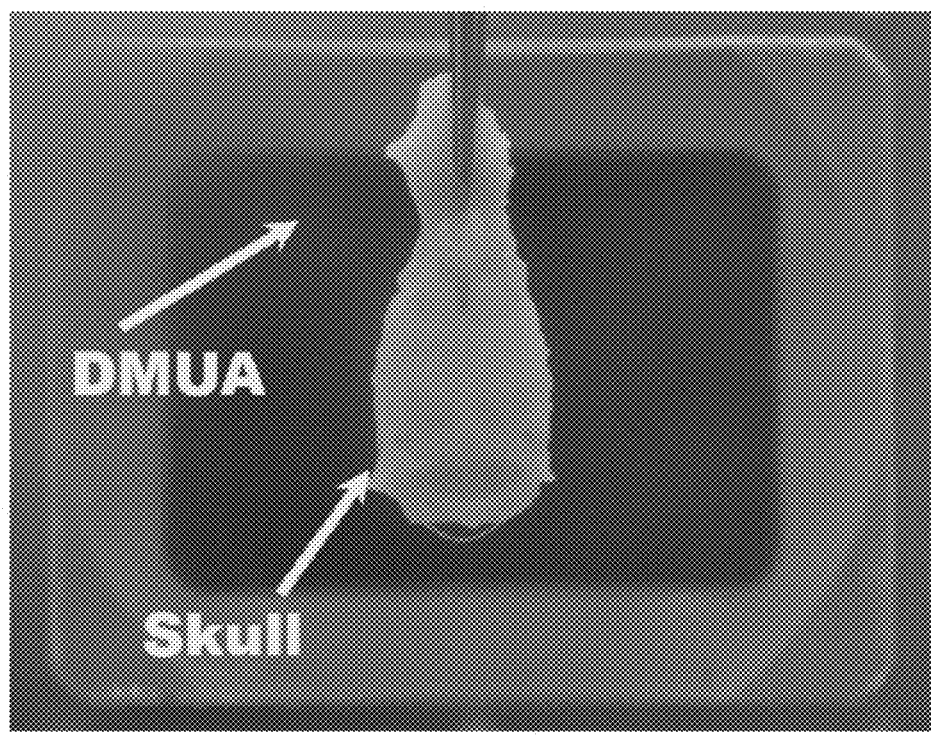
FIGS. 13A-B are images of a setup for hydrophone characterization of trans-skull focusing using a DMUA system.
Figure 13B:
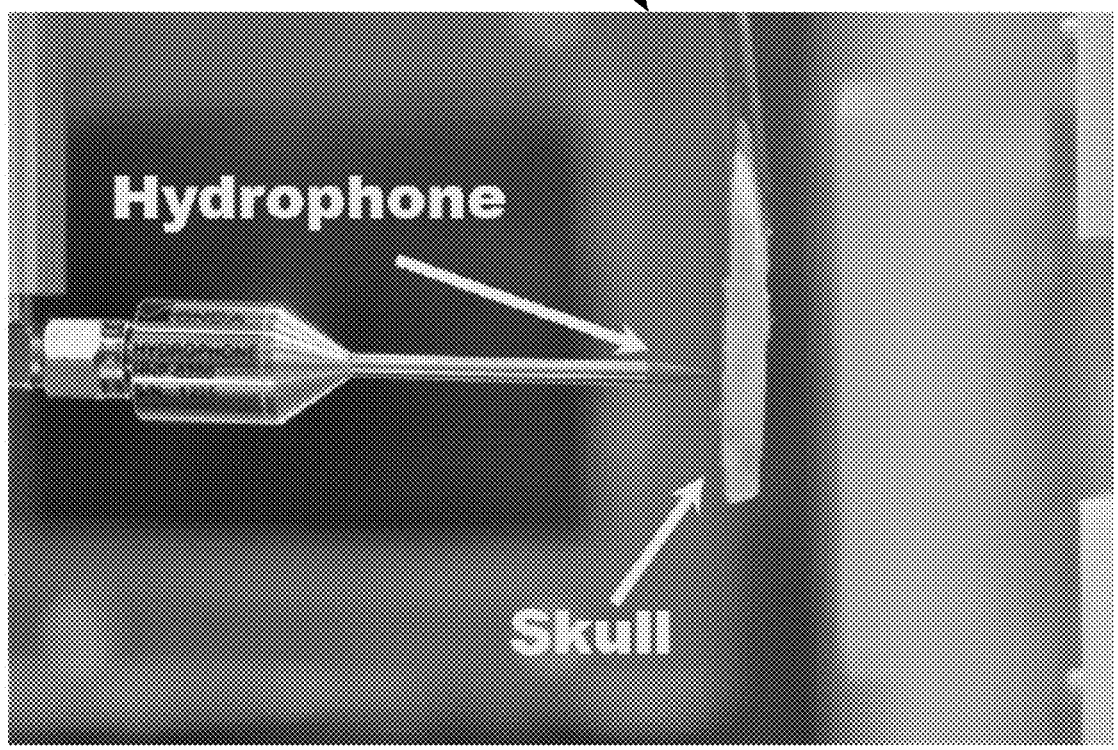

The optimal DMUA designs will be validated using the ex vivo trans-skull characterization setup 950 shown in FIGS. 13A-B, using hydrophone characterization of trans-skull focusing. This setup will facilitate complex measurement of the tFUS beam in a plane parallel to the face of the DMUA. Using backpropagation, the wavefront at the skull surface will be reconstructed, which will define the size of the aperture for the wearable transducer (e.g., patch).

Figures 14A, 14B:
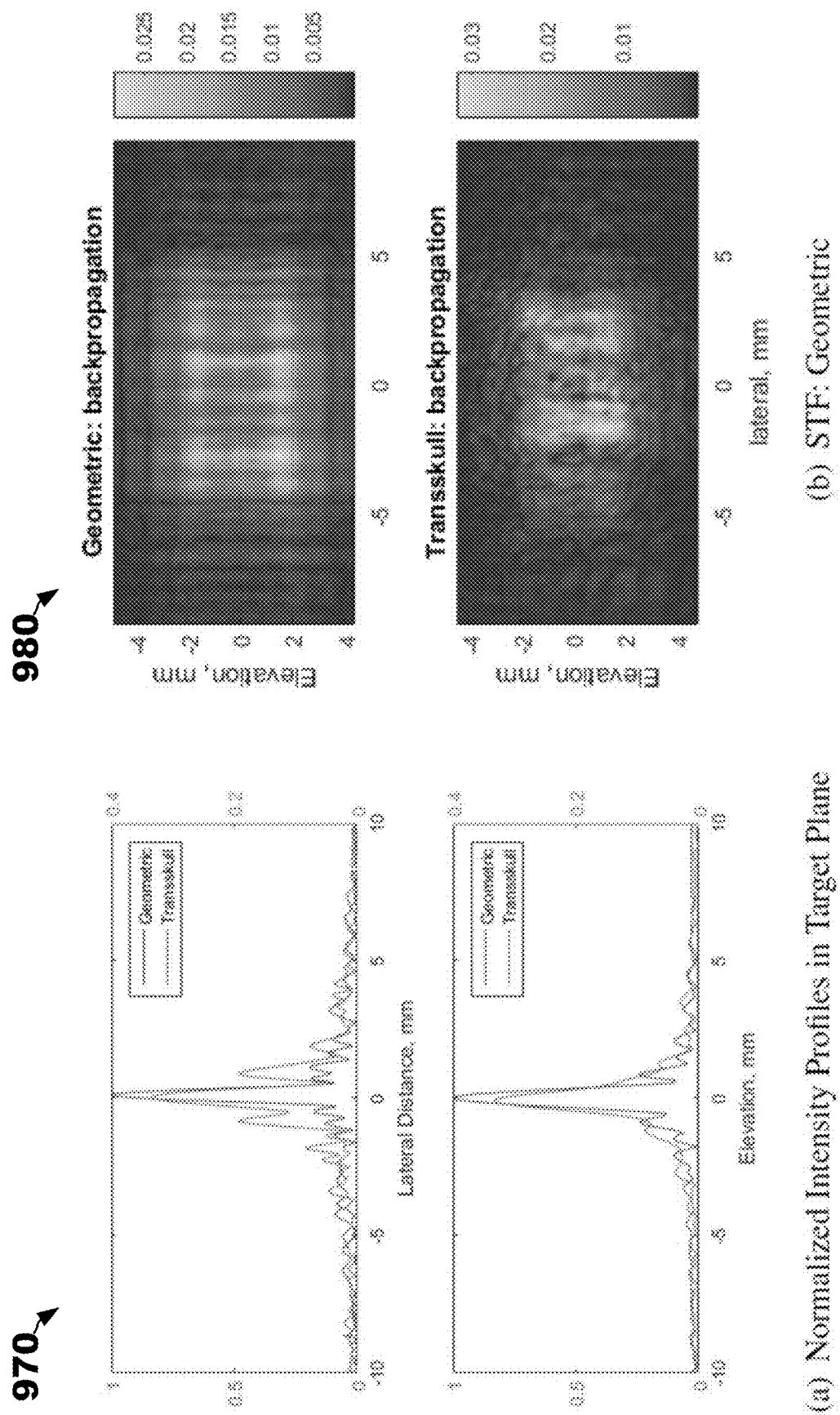
FIGS. 14A-B are plots and profiles showing intensity patterns of FUS in the target plane (FIG. 14A, direct hydrophone measurements) and near the skull surface (FIG. 14B, using back propagation) from using a DMUA system.

FIGS. 14A-B demonstrate the validation method that will be used for estimating the effective aperture of the patch DMUA. The intensity pattern of FUS are shown in the target plane in FIG. 14A, showing direct hydrophone measurements, and near the skull surface in FIG. 14B, showing results of using back propagation. The line plots 970 of FIG. 14A will show normalized lateral and elevation beam profiles of the DMUA geometric focus in water (blue) and trans-skull (red). The results are expected to demonstrate the loss in focusing gain and increased sidelobe level due to the skull. The false color intensity profiles 980 of FIG. 14B will show the backpropagated wavefront at the skull location for water-only (top) and trans-skull (bottom) wavefronts. The latter profile will be used to define the size of the aperture for the wearable ≈5×4 mm² in the lateral and elevation directions.) Furthermore, as illustrated, the energy distribution may be nonuniform within this aperture, which may result in further reduction in the element (channel) count.

Design and Implementation of 3D-Printed Lens Material for Patch DMUA

Use of 3D printing in the fabrication of site-specific acoustic lens material that conforms to the skull geometry in the access region will be investigated. The lens geometry will be derived from the rendered 3D surface of the skull intersecting with the DMUA tFUS beam.

Using a 3D ultrasound imaging approach using existing DMUA prototypes is expected to produce skull surface markers that will be ideal for the identification of treatment sites based on rodent brain atlas, for example, as described in Rembrandt Bakker, Paul Tiesinga, and Rolf Kotter, *The scalable brain atlas: Instant web-based access to public brain atlases and related content*, Neuroinformatics, 13(3): 353-366, 2015, and G Paxinos and KBJ Franklin, *The mouse*

Figure 12:
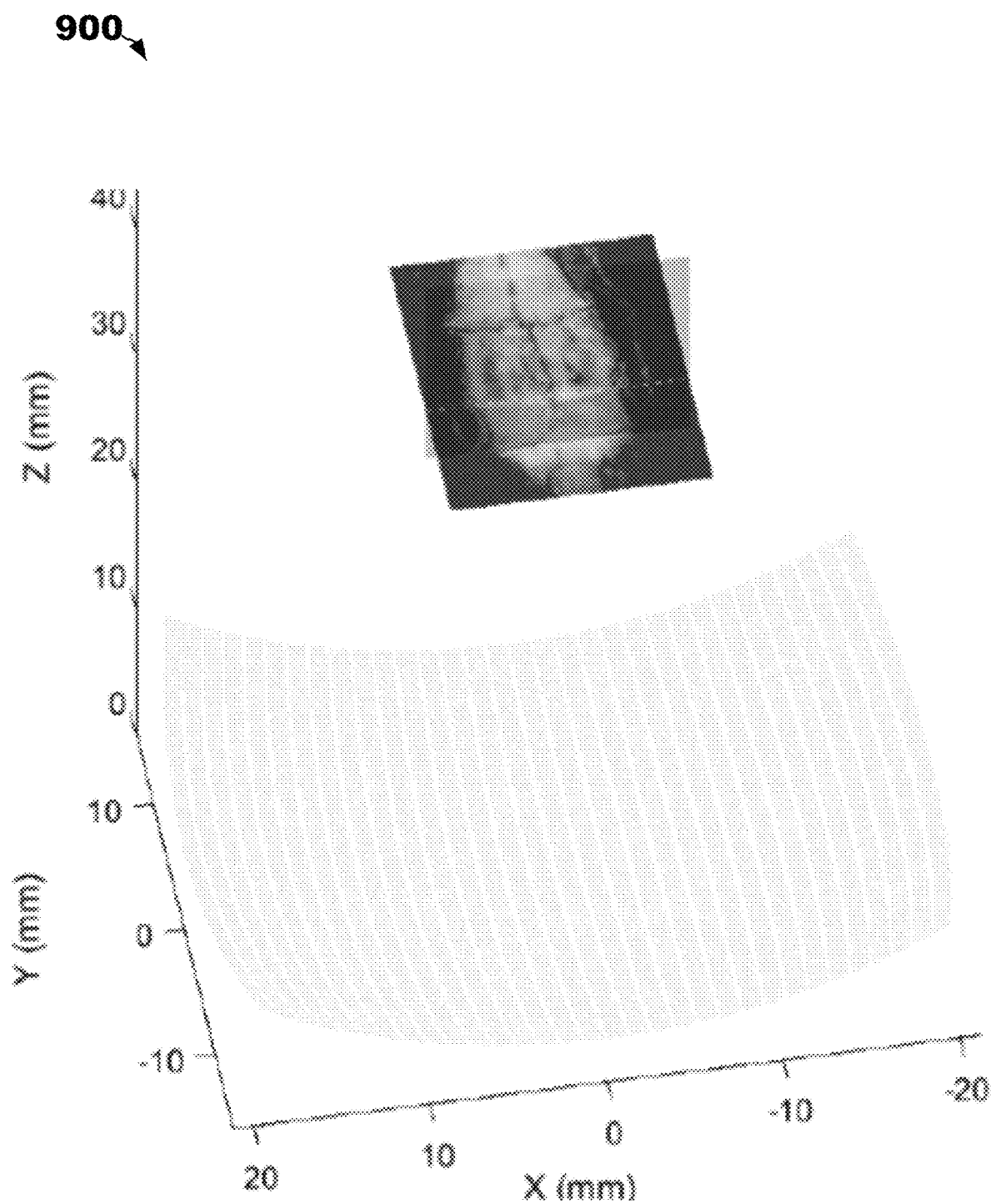
FIG. 12 is a 3 D rendering showing a skull surface in a coordinate system of a DMUA system. In the illustration, the suture lines (bregma, lambda, and medial) may be used as clear markers for placement of the wearable based on DMUA imaging.

*brain in sterotaxic coordinates*, Gulf Professional Publishing, 2004. The skull may be rendered, and its 3D surface can be extracted from the 3D ultrasound render 900 as shown in FIG. 12. In principle, the same methodology can be used to obtain the skull geometry for lens design in larger animals or human subjects. In some cases, 3D imaging data from other modalities such as MM can be used in conjunction with 3D DMUA imaging data. In either case, characterization of transmission through the skull can be achieved using DMUA echo data from the surface of the skull.

Design and Fabrication of Low-Profile PVDF Transducers for Patch DMUAs

A technique for fabricating MR-compatible, low-profile, high-power PVDF transducers as disposable HIFU transducers will be used according to U.S. Pat. No. 6,492,762 (Pant et al.), granted Dec. 10, 2002, entitled "Ultrasonic transducer, transducer array, and fabrication method." Thin slabs of alumina or flexible circuit boards as backing material may be used to lower the resonance frequency and control the operating bandwidths. Efficiency can be increased by using multilayer PVDF films that are connected electrically in parallel and acoustically in series. Efficiencies on the order of 33% are expected achieved, which can be sufficient for a disposable HIFU hyperthermia applicator. The low power operation of requirements for tFUS neuromodulation will even less demanding making the PVDF approach to designing low-profile transducer very attractive for the realization of patch DMUAs.

Experiments will be used to analyze the quality of the transmit and receive signals in typical thermal and nonthermal neuromodulation application. Both will be at the subtherapeutic level, i.e. no ablation.

Thus, various embodiments and examples of WEARABLE TRANSCRANIAL DUAL-MODE ULTRASOUND TRANSDUCERS FOR NEUROMODULATION are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g., 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operably" or "operatively" to describe that the coupling or connection is configured to allow the components to interact to carry out at least some functionality (for example, a processor may be operably coupled to memory to access data stored therein).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all of the listed elements or a combination of at least two of the listed elements.

The phrases "at least one of," "comprises at least one of," and "one or more of" followed by a list refers to any one of the items in the list and any combination of two or more items in the list.

All references and publications cited herein are expressly incorporated herein by reference in their entirety into this disclosure, except to the extent they may directly contradict this disclosure.

What is claimed is:

1. An ultrasound transducer system comprising:
   a lens layer configured to partially or completely compensate for a predetermined ultrasound beam distortion associated with an ultrasound obstacle;
   an ultrasound transducer layer configured to deliver a transmit ultrasound wavefront into the lens layer and to receive a reflected ultrasound wavefront that has passed through the lens layer corresponding to a reflection of the transmit ultrasound wavefront;

a coarse aperture layer coupled to the ultrasound transducer layer and comprising a plurality of channel conductors, wherein each channel conductor is configured to couple to a different portion of a surface of the ultrasound transducer layer, wherein each channel conductor defines a conductive surface area having a size or shape different than at least one other channel conductor, the coarse aperture layer configured to decouple from the ultrasound transducer layer;

a fine aperture layer configured to couple to the ultrasound transducer layer and comprising a greater number of channel conductors than the coarse aperture layer; and a backing layer comprising an electrically insulative material coupled to the coarse aperture layer.

2. The system of claim 1, further comprising a portable control circuit configured to couple to the plurality of channel conductors of the coarse aperture layer, the portable control circuit comprising:

a transmit circuit configured to provide an excitation waveform vector to the plurality of channel conductors to generate the transmit ultrasound wavefront using the ultrasound transducer layer; and a receive circuit configured to receive a reflection waveform vector from the plurality of channel conductors corresponding to the reflected ultrasound wavefront received by the ultrasound transducer layer.

3. The system of claim 1, wherein the conductive surface area of each channel conductor has a size or shape different than all the other channel conductors.

4. The system of claim 1, wherein the fine aperture layer comprises a number of channel conductors equal to at least 10 times the number of channel conductors of the coarse aperture layer.

5. The system of claim 1, further comprising a control circuit configured to couple to the channel conductors of the fine aperture layer.

6. A method using an ultrasound transducer system, comprising:

partially or completely compensating for a predetermined ultrasound beam distortion associated with an ultrasound obstacle using a lens layer;

delivering a transmit ultrasound wavefront into the lens layer and receiving a reflected ultrasound wavefront that has passed through the lens layer corresponding to a reflection of the transmit ultrasound wavefront;

providing a coarse aperture layer coupled to the ultrasound transducer layer and comprising a plurality of channel conductors, wherein each channel conductor is configured to couple to a different portion of a surface of the ultrasound transducer layer, wherein each channel conductor defines a conductive surface area having a size or shape different than at least one other channel conductor, and the coarse aperture layer configured to decouple from the ultrasound transducer layer;

providing a fine aperture layer configured to couple to the ultrasound transducer layer and comprising a greater number of channel conductors than the coarse aperture layer; and providing a backing layer comprising an electrically insulative material coupled to the coarse aperture layer.

7. The method of claim 6, comprising:

providing an excitation waveform vector to the plurality of channel conductors to generate the transmit ultrasound wavefront using the ultrasound transducer layer; and receiving a reflection waveform vector from the plurality of channel conductors corresponding to the reflected ultrasound wavefront received by the ultrasound transducer layer.

8. The method of claim 6, wherein the conductive surface area of each channel conductor has a size or shape different than all the other channel conductors.

9. The method of claim 6, wherein the fine aperture layer comprises a number of channel conductors equal to at least 10 times the number of channel conductors of the coarse aperture layer.

10. The method of claim 6, further comprising operably coupling a control circuit to the channel conductors of the fine aperture layer.

11. An ultrasound transducer system comprising:

a lens layer configured to partially or completely compensate for a predetermined ultrasound beam distortion associated with an ultrasound obstacle;

an ultrasound transducer layer configured to deliver a transmit ultrasound wavefront into the lens layer and to receive a reflected ultrasound wavefront that has passed through the lens layer corresponding to a reflection of the transmit ultrasound wavefront;

a coarse aperture layer coupled to the ultrasound transducer layer and comprising a plurality of channel conductors, wherein each channel conductor is configured to couple to a different portion of a surface of the ultrasound transducer layer, wherein each channel conductor defines a conductive surface area and the conductive surface area of each channel conductor has a size or shape different than all the other channel conductors; and a backing layer comprising an electrically insulative material coupled to the coarse aperture layer.

12. A method using an ultrasound transducer system, comprising:

partially or completely compensating for a predetermined ultrasound beam distortion associated with an ultrasound obstacle using a lens layer;

delivering a transmit ultrasound wavefront into the lens layer and receiving a reflected ultrasound wavefront that has passed through the lens layer corresponding to a reflection of the transmit ultrasound wavefront;

providing a coarse aperture layer coupled to the ultrasound transducer layer and comprising a plurality of channel conductors, wherein each channel conductor is configured to couple to a different portion of a surface of the ultrasound transducer layer, wherein each channel conductor defines a conductive surface area and the conductive surface area of each channel conductor has a size or shape different than all the other channel conductors; and providing a backing layer comprising an electrically insulative material coupled to the coarse aperture layer.

* * * * *